United States Patent
Dudley et al.

(10) Patent No.: US 9,074,185 B2
(45) Date of Patent: Jul. 7, 2015

(54) ADOPTIVE CELL THERAPY WITH YOUNG T CELLS

(71) Applicant: The United States of America, as represented by the Secretary, Department of Health and Human Services, Washington, DC (US)

(72) Inventors: Mark E. Dudley, Washington, DC (US); Steven A. Rosenberg, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 115 days.

(21) Appl. No.: 13/742,541

(22) Filed: Jan. 16, 2013

(65) Prior Publication Data

US 2014/0030806 A1 Jan. 30, 2014

Related U.S. Application Data

(62) Division of application No. 12/869,390, filed on Aug. 26, 2010, now Pat. No. 8,383,099.

(60) Provisional application No. 61/237,889, filed on Aug. 28, 2009.

(51) Int. Cl.
| | |
|---|---|
| *A01N 63/00* | (2006.01) |
| *A61K 35/12* | (2006.01) |
| *A61K 38/00* | (2006.01) |
| *C12N 5/0783* | (2010.01) |
| *A61K 31/675* | (2006.01) |
| *A61K 31/7076* | (2006.01) |
| *A61K 35/17* | (2015.01) |
| *A61K 35/26* | (2015.01) |
| *A61K 38/20* | (2006.01) |
| *A61K 39/00* | (2006.01) |

(52) U.S. Cl.
CPC ............ *C12N 5/0636* (2013.01); *A61K 31/675* (2013.01); *A61K 31/7076* (2013.01); *A61K 35/17* (2013.01); *A61K 35/26* (2013.01); *A61K 38/2013* (2013.01); *A61K 38/2046* (2013.01); *A61K 38/208* (2013.01); *A61K 38/2086* (2013.01); *A61K 2039/515* (2013.01); *C12N 2501/23* (2013.01); *C12N 2501/515* (2013.01)

(58) Field of Classification Search
None
See application file for complete search history.

(56) References Cited

U.S. PATENT DOCUMENTS

| | | |
|---|---|---|
| 8,034,334 B2 | 10/2011 | Dudley et al. |
| 2006/0165652 A1 | 7/2006 | Dudley et al. |
| 2011/0052530 A1 | 3/2011 | Dudley et al. |
| 2011/0268754 A1 | 11/2011 | Dudley et al. |

OTHER PUBLICATIONS

Besser et al., *Clin. Cancer Res.*, 16 (9), 2646-2655 (2010).
Besser et al., *J. Immunother.*, 32 (4), 415-423 (2009).
Clinical Protocol (CC Protocol No. 07-C-0176I).
ClinicalTrials.gov web page ("Tumor-Infiltrating Lymphocytes and High-Dose Aldesleukin After Cyclophosphamide and Fludarabine Phosphate in Patients with Metastatic Melanoma," published Aug. 7, 2007, (http://clinicaltrials.gov/archive/NCT00513604/2007_08_07)).
Cancer.gov web page ("Phase II Study of Tumor-Infiltrating Lymphocytes and High-Dose Aldesleukin After Cyclophosphamide and Fludarabine Phosphate in Patients With Metastatic Melanoma," first published Jul. 24, 2007; last modified Jul. 8, 2009, (http://www.cancer.gov/search/ViewClinicalTrials.aspx?cdrid=557605&version=HealthProfessional&protocolsearchid=6909424)).
Dudley et al., *J. Clin. Oncol.*, 23 (10), 2346-2357 (2005).
Dudley et al., *J. Immunother.*, 26 (4), 332-342 (2003).
Dudley et al., *J. Immunother.*, 25 (3), 243-251 (2002).
Gattinoni et al., *J. Clin. Invest.*, 115 (6), 1616-1626 (2005).
Heemskerk et al., *Hum. Gene Ther.*, 19, 496-510 (2008).
Huang et al., *J. Immunother.*, 28 (3), 258-267 (2005).
Johnson et al., *Blood*, 114 (3), 535-546 (2009).
Powell et al., *Blood*, 105, 241-50 (2005).
Power Point Presentation slides presented by Mark Dudley to the American Society of Clinical Oncology (ASCO), "Clinical Trials with Adoptive Cell Therapy after Prior Lymphodepletion," (Milan, Italy; Mar. 27, 2009).
Power Point slides presented by Mark Dudley to the American Society of Clinical Oncology (ASCO), "Cell Therapy with Lymphodepletion for Patients with Melanoma," (Orlando, Florida; May 30, 2009).
Riddell et al. *J. Immunol. Methods*, 128, 189-201 (1990).
Rosenberg et al., *J. Natl. Cancer Inst.*, 86 (15), 1159-1166 (1994).
Rosenberg et al., *N. England J. Med.*, 319, 1676-1680 (1988).
Shen et al., *J. Immunother.*, 30 (1), 123-129 (2007).
Tran et al., *J. Immunother.*, 31 (8), 742-751 (2008).
Walter et al., *The New England Journal of Medicine*, 333(16), 1038-1044 (Oct. 19, 1995).
Zhou et al., *J. Immunol.*, 175, 7046-7052 (2005).

*Primary Examiner* — Michail Belyavskyi
(74) *Attorney, Agent, or Firm* — Leydig, Voit & Mayer

(57) ABSTRACT

The invention provides a method of promoting regression of a cancer in a mammal comprising (i) culturing autologous T cells; (ii) expanding the cultured T cells; (iii) administering to the mammal nonmyeloablative lymphodepleting chemotherapy; and (iv) after administering nonmyeloablative lymphodepleting chemotherapy, administering to the mammal the expanded T cells, wherein the T cells administered to the mammal are about 19 to about 35 days old and have not been screened for specific tumor reactivity, whereupon the regression of the cancer in the mammal is promoted.

11 Claims, 7 Drawing Sheets

Pre treatment    2 months post

Day -9    Day +11    Day +76

Pre treatment    1 months post

ADOPTIVE CELL THERAPY WITH YOUNG T CELLS

CROSS-REFERENCE TO RELATED APPLICATIONS

This patent application is a divisional of U.S. patent application Ser. No. 12/869,390, filed Aug. 26, 2010, which issued as U.S. Pat. No. 8,383,099, which claims the benefit of U.S. Provisional Patent Application No. 61/237,889, filed Aug. 28, 2009, each of which is incorporated by reference in its entirety.

BACKGROUND OF THE INVENTION

Adoptive cell therapy (ACT) using tumor reactive T-cells following host lymphodepletion can lead to positive, objective, and durable responses in cancer patients. However, this therapy can involve sophisticated cell processing and in vitro lymphocyte culturing for extended periods. These procedures have introduced technical, regulatory, and logistic challenges to the successful use of antigen-specific T cells as a biological therapy. Accordingly, there is a need in the art for improved methods for treating cancer using adoptive cell therapy.

BRIEF SUMMARY OF THE INVENTION

An embodiment of the invention provides a method of promoting regression of a cancer in a mammal comprising (i) culturing autologous T cells; (ii) expanding the cultured T cells using OKT3 antibody, IL-2, and feeder lymphocytes, wherein the cultured T cells are enriched for CD8+ T cells prior to expansion of the T cells; (iii) administering to the mammal nonmyeloablative lymphodepleting chemotherapy; and (iv) after administering nonmyeloablative lymphodepleting chemotherapy, administering to the mammal the expanded T cells, wherein the T cells administered to the mammal are about 19 to about 35 days old and have not been screened for specific tumor reactivity, whereupon the regression of the cancer in the mammal is promoted.

Another embodiment of the invention provides a method of promoting regression of a cancer in a mammal comprising (i) culturing autologous T cells; (ii) expanding the cultured T cells using OKT3 antibody, IL-2, and feeder lymphocytes, wherein the cultured T cells are enriched for CD8+ T cells prior to expansion of the T cells; (iii) administering to the mammal nonmyeloablative lymphodepleting chemotherapy; and (iv) after administering nonmyeloablative lymphodepleting chemotherapy, administering to the mammal the expanded T cells, wherein the T cells administered to the mammal are about 19 to about 29 days old, whereupon the regression of the cancer in the mammal is promoted.

BRIEF DESCRIPTION OF THE SEVERAL VIEWS OF THE DRAWING(S)

Figure 5:
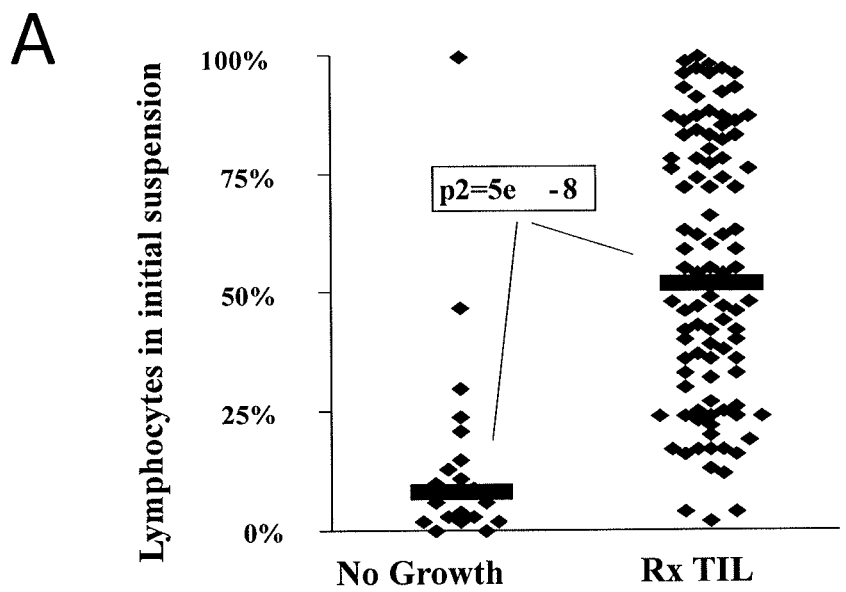
FIG. 5A is a graph showing the percentage of lymphocytes in initial suspension (y axis) for TIL that grew to use for treatment (>5×10$^7$ cells in 28 days, Rx TIL) or TIL for which growth was insufficient for treatment (no growth) (x axis). Black bars indicate median values of the populations. p2=5× 10$^{-8}$.
Figure 5:
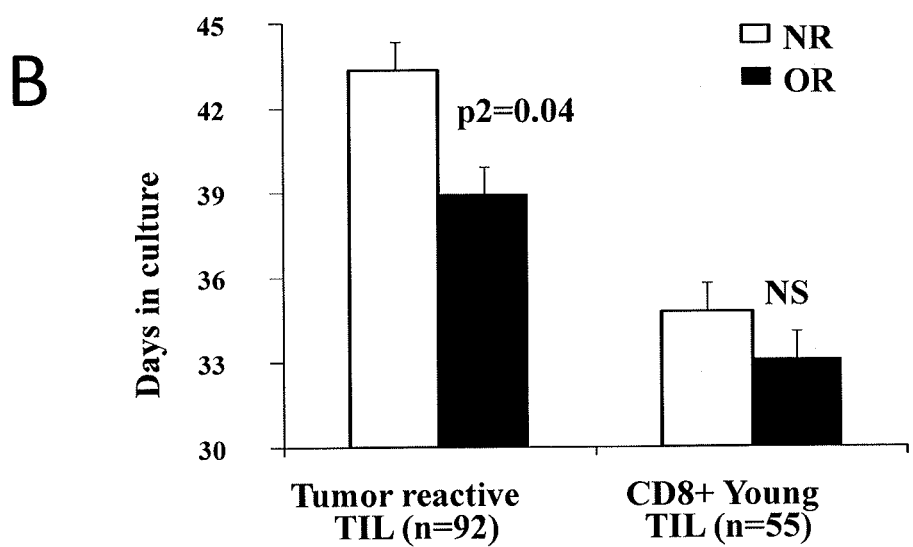

FIG. 5B is a graph showing the number of days in culture (y axis) for TIL in prior protocols in which the TIL underwent individualized testing for tumor reactivity (Specific TIL, n=92) or CD8+ enriched young TIL (CD8+Young TIL, n=55) (x axis) for non-responding (NR) patients (white bars) or objective responders (OR) (black bars). Standard error bars are shown. p2=0.04. NS=not significant.

Figure 6:
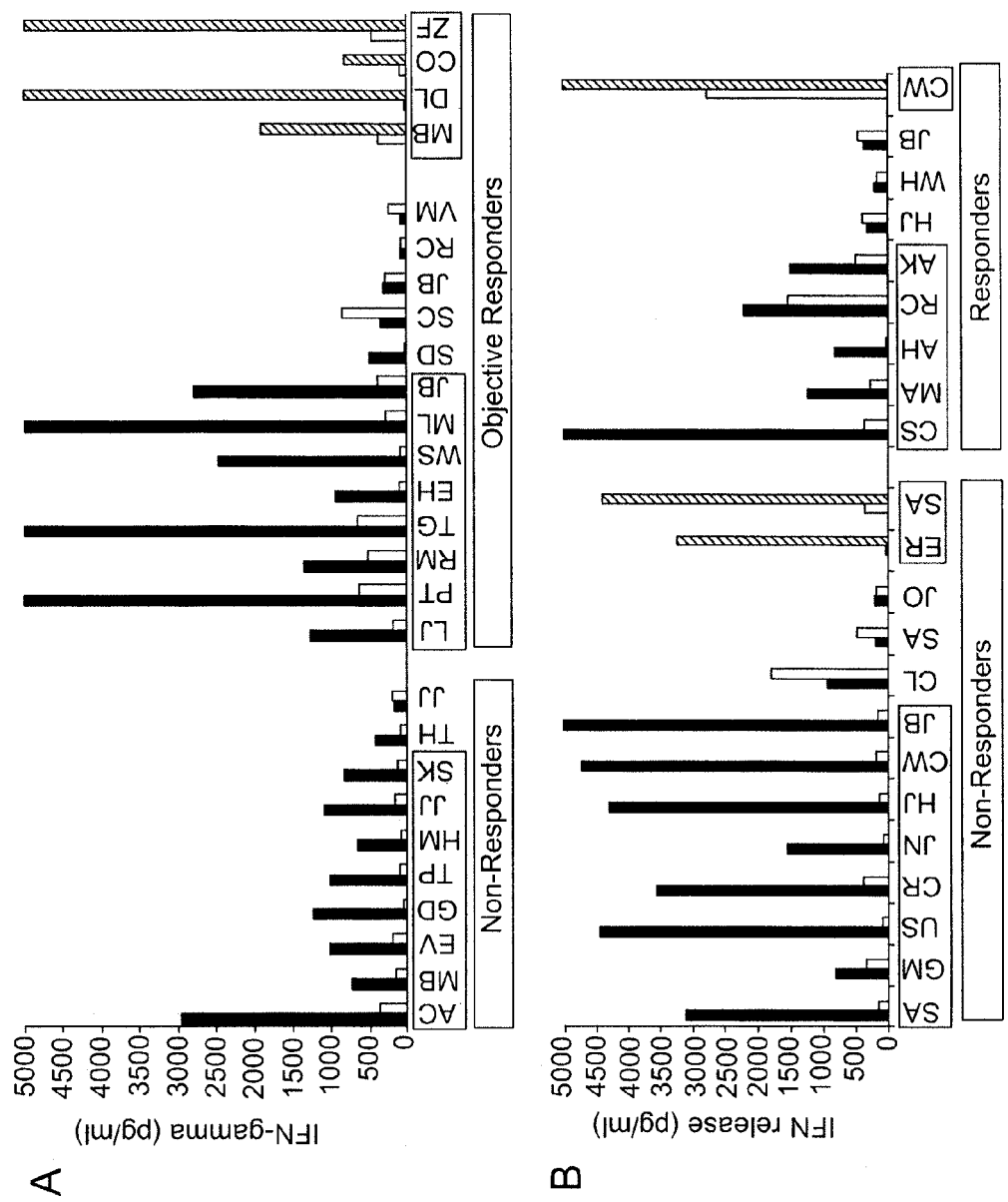

FIG. 6A is a graph showing interferon (IFN)-gamma secretion (pg/ml) (y axis) of CD8+ enriched young TIL administered to patients (x axis) after non-myeloablative chemotherapy (NMA) upon incubation with autologous (black bars), HLA-matched (hatched bars), or HLA-mismatched (white bars) tumors. Patients with specific tumor recognition (greater than 200 pg/ml IFN-gamma and 2×HLA-mismatched tumor) are boxed. Offscale >5000 pg/ml.

FIG. 6B is a graph showing interferon (IFN)-gamma secretion (pg/ml) (y axis) of CD8+ enriched young TIL administered to patients (x axis) after 6Gy total body irradiation (TBI) upon incubation with autologous (black bars), HLA-matched (hatched bars), or HLA-mismatched (white bars) tumors. Patients with specific tumor recognition (greater than 200 pg/ml IFN-gamma and 2×HLA-mis-matched tumor) are boxed. Offscale >5000 pg/ml.

Figure 7:
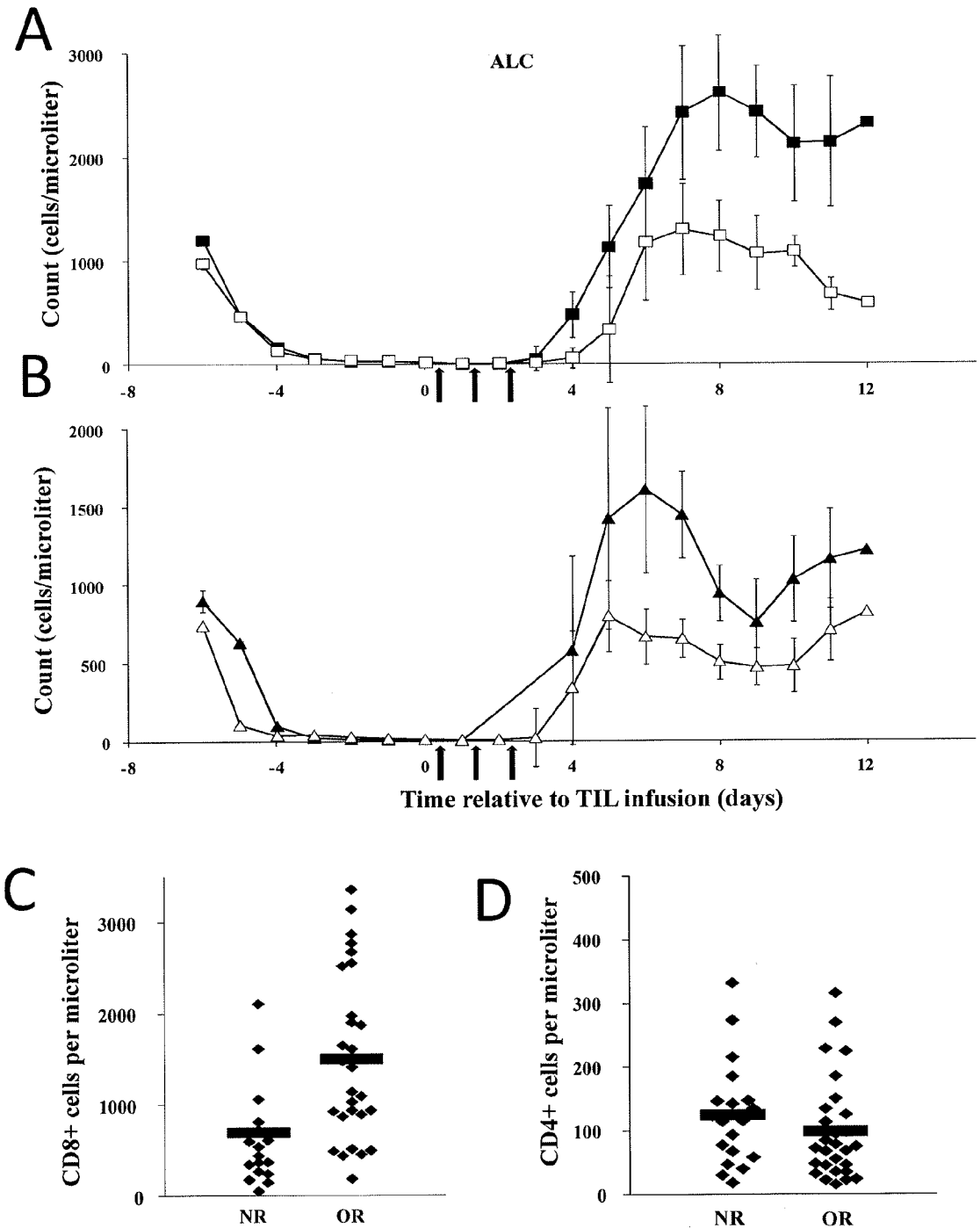

FIG. 7A is a graph showing average absolute lymphocyte cell (ALC) count (cells/microliter) (y axis) for all patients who received CD8+ enriched young TIL with NMA (n=33) (black squares) or all patients who received extensively expanded, tumor selected TIL with NMA as their first treatment (n=33) (historic control) (white squares) over time (days) relative to TIL infusion (x axis). Arrows: IL-2 therapy. Vertical bars: standard error.

FIG. 7B is a graph showing average absolute lymphocyte cell (ALC) count (cells/microliter) (y axis) for all patients who received CD8+ enriched young TIL with 6Gy TBI (n=23) (black triangles) or all patients who received extensively expanded, tumor selected TIL with 12Gy TBI (n=25) (historic control) (white triangles) over time (days) relative to TIL infusion (x axis). Arrows: IL-2 therapy. Vertical bars: standard error.

FIG. 7C is a graph showing CD8+ absolute lymphocyte count (ALC) (cells per microliter) (y axis) for each non-responding (NR) patient or objective responders (OR) (x axis). Black bars: mean ALC for the population. p=0.002.

FIG. 7D is a graph showing CD4+ absolute lymphocyte count (ALC) (cells per microliter) (y axis) for each non-responding (NR) patient or objective responders (OR) (x axis). Black bars: mean ALC for the population. p=0.5.

DETAILED DESCRIPTION OF THE INVENTION

An embodiment of the present invention provides a method of promoting the regression of a cancer in a mammal. The method comprises (i) culturing autologous T cells; (ii) expanding the cultured T cells using OKT3 antibody, IL-2, and feeder lymphocytes, wherein the cultured T cells are enriched for CD8+ T cells prior to expansion of the T cells; (iii) administering to the mammal nonmyeloablative lymphodepleting chemotherapy; and (iv) after administering nonmyeloablative lymphodepleting chemotherapy, administering to the mammal the expanded T cells, wherein the T cells administered to the mammal are about 19 to about 35 days old and have not been screened for specific tumor reactivity, whereupon the regression of the cancer in the mammal is promoted. In some embodiments, the administered T cells are less than about 35 days old, e.g., about 19 to about 26 days old.

The inventive methods provide numerous advantages. For example, T cells that are about 19 to about 35 days old are believed to provide improved in vivo proliferation, survival, and antitumor activity as compared to T cells that are about 44 days old or older. In addition, because the inventive methods include nonmyeloablative chemotherapy, the inventive methods can advantageously be used to treat patients that would not be eligible for treatments that involve total body irradiation (TBI) such as, for example, patients that have already undergone myeloablative therapy, e.g., radiotherapy, prior to treatment; patients with comorbid conditions; and patients with less than $2 \times 10^6$ CD34$^+$ cells/kg. Moreover, the period of time required to generate T cells for adoptive cell therapy (ACT) may be shortened from an average of about 44 days to a range of about 19 to about 35 days (or less than about 35 days, e.g., about 19 to about 29 days, or about 19 to about 26 days). Accordingly, more patients may be treated before their disease burden progresses to a stage in which administration of ACT may no longer be safe or possible. Furthermore, because preferred embodiments of the inventive methods do not require in vitro testing of specific antigen reactivity prior to administration, the inventive methods reduce the time, expense, and labor associated with the treatment of patients. Additionally, the inventive methods may advantageously administer T cells that are pooled from bulk cultures instead of those derived from microcultures. The development of a simpler and faster method to generate clinically effective T cells is believed to aid in the more widespread use of adoptive cell therapy. The inventive methods also advantageously utilize T cell cultures that could be falsely predicted to be unreactive in vivo by in vitro testing of specific antigen reactivity. Because T cell cultures generated from a single tumor specimen have diverse specific reactivities, the lack of in vitro antigen reactivity testing advantageously avoids having to choose only a few T cell cultures to expand, and therefore provides a more diverse repertoire of tumor reactivities to be administered to the patient. T cells that are about 19 to about 35 days old also contain a greater diversity of cells and a higher frequency of CD4$^+$ cells than T cells that are about 44 days old. In addition, one or more aspects (e.g., but not limited to, culturing and/or expanding) of the inventive methods may be automatable.

An embodiment of the method comprises culturing autologous T cells. Tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2), e.g., in multiple wells. The cells are cultured until confluence (e.g., about $2 \times 10^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, preferably from 10 days, 10.5 days, or 10.8 days to 14 days, 14.5 days, or 14.8 days.

An embodiment of the method comprises expanding cultured T cells. The cultured T cells are pooled and rapidly expanded. Rapid expansion provides an increase in the number of antigen-specific T-cells of at least about 50-fold (e.g., 50-, 60-, 70-, 80-, 90-, or 100-fold, or greater) over a period of about 10 to about 14 days, preferably about 14 days. More preferably, rapid expansion provides an increase of at least about 200-fold (e.g., 200-, 300-, 400-, 500-, 600-, 700-, 800-, 900-, or greater) over a period of about 10 to about 14 days, preferably about 14 days. Most preferably, rapid expansion provides an increase of at least about 1000-fold over a period of about 10 to about 14 days, preferably about 14 days. Preferably, rapid expansion provides an increase of about 1000-fold over a period of about 14 days.

Expansion can be accomplished by any of a number of methods as are known in the art. For example, T cells can be rapidly expanded using non-specific T-cell receptor stimulation in the presence of feeder lymphocytes and either interleukin-2 (IL-2) or interleukin-15 (IL-15), with IL-2 being preferred. The non-specific T-cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, e.g., 0.3 µM MART-1:26-35 (27 L) or gp100:209-217 (210M), in the presence of a T-cell growth factor, such as 300 IU/ml IL-2 or IL-15, with IL-2 being preferred. The in vitro-induced T-cells are rapidly expanded by re-stimulation with the same antigen(s) of the cancer pulsed onto HLA-A2-expressing antigen-presenting cells. Alternatively, the T-cells can be restimulated with irradiated, autologous lymphocytes or with irradiated HLA-A2+ allogeneic lymphocytes and IL-2, for example.

An embodiment of the method comprises administering to the mammal nonmyeloablative lymphodepleting chemotherapy. The nonmyeloablative lymphodepleting chemotherapy can be any suitable such therapy, which can be administered by any suitable route. The nonmyeloablative lymphodepleting chemotherapy can comprise, for example, the administration of cyclophosphamide and fludarabine, particularly if the cancer is melanoma, which can be metastatic. A preferred route of administering cyclophosphamide and fludarabine is intravenously. Likewise, any suitable dose of cyclophosphamide and fludarabine can be administered. Preferably, around 60 mg/kg of cyclophosphamide is administered for two days after which around 25 mg/m$^2$ fludarabine is administered for five days, particularly if the cancer is melanoma.

An embodiment of the method comprises, after administering the nonmyeloablative lymphodepleting chemotherapy, administering to the mammal the expanded T cells, wherein the T cells administered to the mammal are about 19 to about 35 days old. For example, the administered cells may be 19, 19.5, or 19.8 to 35, 35.5, or 35.8 days old. In some embodiments, the T cells administered to the mammal are about 19 to about 29 or about 23 to about 29 days old, or about 26 days old. For example, the administered cells may be 19, 19.5, or 19.8 to 29, 29.5, or 29.8 days old; 23, 23.5, or 23.8 to 29, 29.5, or 29.8 days old; or 26, 26.5, or 26.8 days old. In this regard, the T cells that are administered to the mammal according to an embodiment of the invention are "young" T cells, i.e., minimally cultured T cells.

Young T cell cultures that are administered to the mammal in accordance with an embodiment of the invention advantageously have features associated with in vivo persistence, proliferation, and antitumor activity. For example, young T cell cultures have a higher expression of CD27 and/or CD28 than T cells that are about 44 days old. Without being bound to a particular theory, it is believed that CD27 and CD28 are associated with proliferation, in vivo persistence, and a less differentiated state of T cells (the increased differentiation of T cells is believed to negatively affect the capacity of T cells to function in vivo). T cells expressing higher levels of CD27 are believed to have better antitumor activity than CD27-low cells. Moreover, young T cell cultures have a higher frequency of CD4$^+$ cells than T cells that are about 44 days old.

In addition, young T cell cultures have a mean telomere length that is longer than that of T cells that are about 44 days old. Without being bound to a particular theory, it is believed that T cells lose an estimated telomere length of 0.8 kb per week in culture, and that young T cell cultures have telomeres that are about 1.4 kb longer than T cells that are about 44 days old. Without being bound to a particular theory, it is believed that longer telomere lengths are associated with positive objective clinical responses in patients and persistence of the cells in vivo.

The T-cells can be administered by any suitable route as known in the art. Preferably, the T-cells are administered as an intra-arterial or intravenous infusion, which preferably lasts about 30 to about 60 minutes. Other examples of routes of administration include intraperitoneal, intrathecal and intra-lymphatic.

Likewise, any suitable dose of T-cells can be administered. Preferably, from about $1.0 \times 10^{10}$ T-cells to about $13.7 \times 10^{10}$ T-cells are administered, with an average of around $5.0 \times 10^{10}$ T-cells, particularly if the cancer is melanoma. Alternatively, from about $1.2 \times 10^{10}$ to about $4.3 \times 10^{10}$ T-cells are administered.

In a preferred embodiment, the T cells are not tested for specific tumor reactivity to identify tumor reactive T cells prior to administration to the patient. Specific tumor reactivity can be tested by any method known in the art, e.g., by measuring cytokine release (e.g., interferon-γ) following co-culture with tumor cells. The inventive methods advantageously make it possible to promote regression of cancer in a mammal by administering T cells to the mammal without the necessity of prior screening for specific tumor recognition. Embodiments of the methods may, if desired, test the T cells for potency in a non-antigen-specific manner prior to administering the T cells to the mammal. T cell potency may be tested, e.g., by a non-specific potency assay measuring cytokine release following OKT3 stimulation. T cells may be considered potent if, for example, interferon (IFN) release is greater than about 50 pg/mL, greater than about 100 pg/mL, greater than about 150 pg/mL, or greater than about 200 pg/mL. A less desired embodiment of the method comprises testing the expanded T cells for specific tumor reactivity to identify tumor-reactive T cells.

Another embodiment of the invention provides a method of promoting regression of a cancer in a mammal comprising (i) culturing autologous T cells; (ii) expanding the cultured T cells using OKT3 antibody, IL-2, and feeder lymphocytes, wherein the cultured T cells are enriched for CD8+ T cells prior to expansion of the T cells; (iii) administering to the mammal nonmyeloablative lymphodepleting chemotherapy; and (iv) after administering nonmyeloablative lymphodepleting chemotherapy, administering to the mammal the expanded T cells, wherein the T cells administered to the mammal are about 19 to about 29 days old, whereupon the regression of the cancer in the mammal is promoted. For example, the T cells administered to the mammal may be 19, 19.5, 19.8 to 29, 29.5, or 29.8 days old. An embodiment of the method comprises culturing autologous T cells as described herein from about 5 days to about 15 days. For example, the T cells may be cultured from 5, 5.5, or 5.8 days to 15, 15.5, or 15.8 days. The method further comprises expanding the cultured T cells and administering to the mammal nonmyeloablative lymphodepleting chemotherapy as described herein. After administering nonmyeloablative lymphodepleting chemotherapy, the method comprises administering to the mammal the expanded T cells as described herein, whereupon the regression of the cancer in the mammal is promoted. In a preferred embodiment of the method, the administered T cells have not been screened for specific tumor reactivity.

An embodiment of the method comprises enriching cultured T cells for CD8$^+$ T cells prior to rapid expansion of the cells. Following culture of the T cells in IL-2, the T cells are depleted of CD4$^+$ cells and enriched for CD8$^+$ cells using, for example, a CD8 microbead separation (e.g., using a CliniMACS$^{plus}$ CD8 microbead system (Miltenyi Biotec)). Without being bound to a particular theory, it is believed that CD4$^+$, CD25$^+$ regulatory T-cells can impede anti-tumor responses. Accordingly, it is believed that enriching cultured T cells for CD8$^+$ T cells and reducing or eliminating CD4$^+$ cells may improve the impact of adoptively transferred anti-tumor CD8$^+$ cells, improve the response rates in patients, and/or reduce the toxicities seen by production of cytokines by CD4$^+$ cells. Moreover, it is believed that CD8$^+$ enrichment of some T cell cultures reveals in vitro tumor recognition that may not be evident in the bulk culture, and improved in vitro recognition of tumor in other cultures. Additionally, the enriched CD8+ young T cells are believed to behave more reliably and predictably in clinical scale rapid expansions than the bulk T cells.

In an embodiment of the method, a T-cell growth factor that promotes the growth and activation of the autologous T cells is administered to the mammal either concomitantly with the autologous T cells or subsequently to the autologous T cells. The T-cell growth factor can be any suitable growth factor that promotes the growth and activation of the autologous T-cells. Examples of suitable T-cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T-cell growth factor.

In an embodiment of the method, the autologous T-cells are modified to express a T-cell growth factor that promotes the growth and activation of the autologous T-cells. Suitable T-cell growth factors include, for example, any of those described above. Suitable methods of modification are known in the art. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Desirably, modified autologous T-cells express the T-cell growth factor at high levels. T-cell growth factor coding sequences, such as that of IL-12, are readily available in the art, as are promoters, the operable linkage of which to a T-cell growth factor coding sequence promote high-level expression.

In some embodiments, it is believed, two cytokines are more effective than a single cytokine, and three cytokines, e.g., IL-2, IL-7 and IL-15, are better than any two cytokines. It is believed that IL-15 enhances a tumor-specific CD8+ T-cell response. In this regard, the administration of IL-15-cultured cells with IL-2 (such as a bolus injection) can be particularly efficacious.

The T-cell growth factor can be administered by any suitable route. If more than one T-cell growth factor is administered, they can be administered simultaneously or sequentially, in any order, and by the same route or different routes. Preferably, the T-cell growth factor, such as IL-2, is administered intravenously as a bolus injection. Desirably, the dosage of the T-cell growth factor, such as IL-2, is what is considered by those of ordinary skill in the art to be high. Preferably, a dose of about 720,000 IU/kg of IL-2 is administered three times daily until tolerance, particularly when the cancer is melanoma. Preferably, about 5 to about 15 doses of IL-2 are administered, with an average of around 9 doses.

T-cells can recognize any of the unique antigens produced as a result of the estimated 10,000 genetic mutations encoded by each tumor cell genome. The antigen, however, need not be unique. T-cells can recognize one or more antigens of a cancer, including an antigenic portion of one or more antigens, such as an epitope, or a cell of the cancer. An "antigen of a cancer" and an "antigen of the cancer" are intended to encompass all of the aforementioned antigens. If the cancer is melanoma, such as metastatic melanoma, preferably the T-cells recognize MART-1 (such as MART-1:26-35 (27 L)), gp100 (such as gp100:209-217 (210M)), or a "unique" or patient-specific antigen derived from a tumor-encoded mutation. Other suitable melanoma antigens which may be recognized by T-cells can include, but are not limited to, NY-ESO-1, tyrosinase tumor antigen, tyrosinase related protein (TRP)-1, TRP-2, VEGFR-2, and a member of the MAGE family of proteins, e.g., MAGE-A1, MAGE A2, MAGE-A3, MAGE-A6, and MAGE 12. T cells can also recognize antigens such as, for example, telomerase, p53, HER2/neu, mesothelin, carcinoembryonic antigen, or prostate-specific antigen, for treatment of lung carcinoma, breast cancer, colon cancer, prostate cancer, and the like.

In an embodiment of the method, the autologous T-cells are modified to express a T cell receptor (TCR) having antigenic specificity for a cancer antigen, e.g., any of the cancer antigens described herein. Suitable TCRs include, for example, those with antigenic specificity for a melanoma antigen, e.g., gp100 or MART-1. Suitable methods of modification are known in the art. See, for instance, Sambrook and Ausubel, supra. For example, the T cells may be transduced to express a T cell receptor (TCR) having antigenic specificity for a cancer antigen using transduction techniques described in Heemskerk et al. *Hum Gene Ther.* 19:496-510 (2008) and Johnson et al. *Blood* 114:535-46 (2009).

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the vulva, chronic lymphocytic leukemia, chronic myeloid cancer, cervical cancer, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, peritoneum, omentum, and mesentery cancer, pharynx cancer, prostate cancer, rectal cancer, renal cancer, skin cancer, soft tissue cancer, testicular cancer, thyroid cancer, ureter cancer, urinary bladder cancer, and digestive tract cancer such as, e.g., esophageal cancer, gastric cancer, pancreatic cancer, stomach cancer, small intestine cancer, gastrointestinal carcinoid tumor, cancer of the oral cavity, colon cancer, and hepatobiliary cancer. A preferred cancer is melanoma. A particularly preferred cancer is metastatic melanoma.

As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The term "regression," as well as words stemming therefrom, as used herein, does not necessarily imply 100% or complete regression. Rather, there are varying degrees of regression of which one of ordinary skill in the art recognizes as having a potential benefit or therapeutic effect. In this respect, the inventive methods can provide any amount of any level of regression of cancer in a mammal. Furthermore, the regression provided by the inventive method can include regression of one or more conditions or symptoms of the disease, e.g., cancer. Also, for purposes herein, "regression" can encompass delaying the onset of the disease, or a symptom or condition thereof.

The following examples further illustrate the invention but, of course, should not be construed as in any way limiting its scope.

Comparative Example 1

This example demonstrates the generation of "standard" tumor-infiltrating lymphocytes (TIL).

"Standard" TIL were generated as generally described in Example 1 (set out after the Comparative Examples below), except that a standard TIL culture would be cultured to generate $5 \times 10^7$ lymphocytes from each original well of tumor fragment or digest after 21-36 days. Standard TIL were propagated by splitting an individual confluent well into two daughter wells, and maintaining each initial fragment or well of digest as an independent culture. Each standard TIL culture was split multiple times until it comprised confluent growth of 24 daughter wells generated from one original 2-ml well. TIL were assayed for activity when the culture generated $5 \times 10^7$ lymphocytes from each original well of tumor fragment or digest (after 21-36 days).

Specific reactivity of TIL was assessed by interferon-γ (IFN-γ) release assay. TIL were washed prior to use to remove IL-2, then cultured overnight with autologous, HLA-matched, or HLA-mismatched tumor cells at a ratio of 1:1. Single cell suspensions of fresh tumor digests were prepared as targets from autologous or allogeneic melanoma specimens by overnight digestion of macerated tumor fragments in media containing collagenase, hyaluronidase, and DNAse. The single cell suspension was washed twice with HBSS and aliquots were cryopreserved. Targets were thawed on the day of coculture, and viable tumor cells were assessed by trypan blue exclusion. The supernatant from each coculture was then assayed for IFN-γ by ELISA (Pierce/Endogen) according to the manufacturer recommendations. A TIL culture was defined as possessing specific reactivity if IFN-γ release was twice background (coculture of TIL with HLA-mismatched tumors) and at least 200 pg/mL unless otherwise noted.

Rapid expansion was performed as described in Example 1.

This example demonstrated the generation of "standard" tumor-infiltrating lymphocytes (TIL).

Comparative Example 2

This example demonstrates that tests for in vitro reactivity may underestimate the number of tumor-reactive TIL cultures.

When multiple independent TIL cultures are generated from a single melanoma tumor and screened for tumor recognition they often exhibit multiple patterns of reactivity. A representative example from an HLA-A2+ patient is shown in Table 1. In this example, six independent TIL cultures were generated from tumor fragments (F1-F6) and four independent TIL cultures were generated from enzymatic single cell digests (D1-D4) of one melanoma tumor as described in Comparative Example 1. All cultures were the same age and were evaluated in the same coculture assay. When stimulated with HLA-A2+ and HLA-negative melanoma lines, five of the ten independent TIL cultures (50%) had specific reactivity by objective criteria (IFNγ release that was greater than 200 pg/ml and more than twice the highest HLA-mismatched control). No autologous tumor cell line was available from this patient, but when the TIL cultures were stimulated with uncultured autologous tumor cells and HLA-mismatched tumor cell controls, seven of ten independent TIL cultures (70%) had specific reactivity. Some TIL cultures recognized one source of tumor antigen but not the other source, suggesting the presence of multiple antigen reactive lymphocyte populations in these TIL cultures.

TABLE 1

| TIL* | Melanoma Cell Line | | | | | Fresh Tumor | | | |
|---|---|---|---|---|---|---|---|---|---|
| | 888 | 938 | 526 | 624 | | 2515 | 2547 | Auto- | |
| A2+ | A2− | A2− | A2+ | A2+ | Reactivity† | A2− | A2− | logous | Reactivity |
| | IFNg (pg/ml) | | | | | IFNg (pg/ml) | | | |
| F1 | 49 | 63 | 73 | 120 | − | 73 | 193 | 377 | − |
| F2 | 83 | 69 | 1470 | 1676 | + | 63 | 79 | 360 | + |
| F3 | 40 | 62 | 71 | 95 | − | 55 | 45 | 268 | + |
| F4 | 51 | 44 | 122 | 230 | + | 81 | 101 | 206 | + |
| F5 | 35 | 35 | 84 | 248 | + | 48 | 56 | 94 | − |
| F6 | 13 | 16 | 19 | 22 | − | 16 | 100 | 162 | − |
| D1 | 66 | 44 | 394 | 395 | + | 175 | 488 | 3340 | + |
| D2 | 77 | 52 | 140 | 140 | − | 257 | 552 | 5380 | + |
| D3 | 280 | 224 | 1561 | 1420 | + | 528 | 1394 | 4870 | + |
| D4 | 168 | 145 | 200 | 269 | − | 350 | 902 | 3110 | + |
| Total positive (%) | | | | | 5 (50) | | | | 7 (70) |

*Results for ten independent TIL cultures derived from a single tumor from an HLA-A2+ patient are shown. Six cultures prefixed by an "F" were derived from tumor fragments and four cultures prefixed by a "D" were derived from enzymatically-prepared digests.
†Bold numbers indicate a positive test defined as at least 200 pg/mL and greater than twice IFN-γ released by coculture with HLA-mismatched controls. The TIL culture was considered reactive if either HLA-matched target was positive.

Some TIL cultures do not specifically recognize HLA-matched melanoma cell lines, but do recognize autologous tumor cells (such as F3, D2, and D4 in Table 1).

This example demonstrated that tests for in vitro reactivity may underestimate the number of tumor-reactive TIL cultures.

Comparative Example 3

This example demonstrates that tests for in vitro reactivity may underestimate the number of tumor-reactive TIL cultures.

The initial results from a cytokine release assay for several TIL cultures from a patient with a large, inoperable scalp lesion and multiple lung metastases showed no reactivity against HLA-matched tumor lines as targets. In this assay no autologous tumor cells were available. Since no reactive TIL were available, the patient was discharged from the protocol and the TIL cultures were cryopreserved. After several additional weeks, an autologous tumor cell line was established. When the TIL were thawed and the autologous tumor was used as a target, it revealed significant tumor specific recognition by several cultures, including TIL F7. The patient was contacted and consented to receive the F7 TIL cells with high dose IL-2 following a non-myeloablative lymphodepleting preparative chemotherapy on the experimental clinical protocol (Dudley et al. *J. Clin. Oncol.* 23:2346-57 (2005)). The patient experienced a dramatic regression of tumor at all sites and has an ongoing objective response now more than three years after initial TIL treatment. Without the appropriate autologous tumor target cells, the F7 TIL culture could not have been used for treatment in this protocol, which requires evidence of tumor recognition as part of the certificate of release for the cell product.

This example demonstrated that tests for in vitro reactivity may underestimate the number of tumor-reactive TIL cultures.

Comparative Example 4

This example demonstrates that tests for in vitro reactivity may underestimate the number of tumor-reactive TIL cultures.

To quantify the potential clinical impact of autologous tumor target availability, we undertook a retrospective analysis of sequential melanoma samples (Table 2).

TABLE 2

|  | Patients (% of total) | Tumors (% of total) |
|---|---|---|
| Tissue received in Cell Processing Facility | 83 (100%) | 142 (100%) |
| One or more independent TIL culture growth to >10 million cells[1] | 72 (87%) | 116 (82%) |
| Shared melanoma Ag recognition (HLA matched tumor cell line recognition[2]) | 30 (36%) | 40 (26%) |
| Unique Ag recognition (autologous cryopreserved tumor recognition) | 11 (13%) | 21 (15%) |
| Total TIL available for treatment | 41 (49%) | 61 (43%) |

[1]Growth positive TIL was considered 10 million cells from any single independent culture. Typically 20 to 50 million cells were obtained in 3 to 4 weeks.
[2]Tumor recognition was defined by IFNγ release assay with specific release being greater than 200 pg/ml and twice background.

During this ten month period, 142 tumors were processed from 83 patients. TIL failed to grow from 26 tumors, resulting in 11 patients who had no TIL to screen for tumor reactivity. TIL cultures were successfully screened by coculture assay and IFNγ ELISA from one or more independent TIL culture from the remaining 116 tumors from 72 patients, including 49 HLA-A2 patients. Forty tumors (26%) from 30 different patients (36%) exhibited specific recognition of HLA-matched melanoma tumor lines, including 24 HLA-A2+ patients and six HLA-A2 negative patients. Additional specific tumor recognition was revealed for 21 tumors (15%) from 11 patients (13%) by using autologous tumor cells as stimulator cells in cytokine release assays. These data emphasize that tests for in vitro reactivity may underestimate the number of tumor-reactive TIL cultures unless ideal tumor target cells are available. Based in part on these results, we initiated an investigation of alternative strategies for the production of TIL cultures for use in ACT trials, including the use of early TIL cultures with untested antigen reactivities.

This example demonstrated that tests for in vitro reactivity may underestimate the number of tumor-reactive TIL cultures.

Example 1

This example demonstrates the generation of "young" tumor-infiltrating lymphocytes (TIL).

Patients were entered into clinical protocols and signed informed consents that were approved by the Institutional Review Board of the National Cancer Institute prior to tumor resection. TIL were prepared as previously described in detail (Dudley et al. *J. Immunother.* 26:332-42 (2003)). Briefly, multiple independent TIL cultures were set up using enzymatic digests and tumor fragments (1 mm$^3$) procured by sharp dissection. TIL from tumor digests were generated by culturing single-cell suspensions ($5 \times 10^5$/ml) obtained by overnight enzymatic digestion of tumor fragments in media containing collagenase, hyaluronidase, and DNAse. Fragments and digests were initiated in 2 ml wells of complete medium (CM) and IL2 (6000 IU/ml, Chiron Corp., Emeryville, Calif.) in a humidified 37° C. incubator with 5% $CO_2$. CM consisted of RPMI1640 with glutamine, plus 10% human AB serum, 25 mM HEPES, 10 μg/ml gentamicin, and $5.5 \times 10^{-5}$M 2-mercaptoethanol. Five days after initiation, one half of the media was aspirated from the wells and replaced with fresh CM and IL-2, and media was replaced every two to three days thereafter as needed. Under these conditions, lymphocytes will first lyse the adherent cells in the well, and then begin to multiply and grow.

Young TIL were defined as cultures which had just expanded to confluent growth of the original 2-ml well and eliminated adherent tumor cells, typically about 10-18 days after initiation. In practice, this was about $2 \times 10^6$ lymphocytes from each original tumor fragment or digest well. By pooling all the wells in a single 24 well plate, approximately $5 \times 10^7$ young TIL cells would be obtained.

Rapid expansions of the culture was performed using the Rapid Expansion Protocol (REP) as previously described (Dudley et al. *J. Immunother.* 26:332-42 (2003) and Riddell et al. *J. Immunol. Methods* 128:189-201 (1990)). Briefly, TIL cells were cultured in T25 flasks with a 200 fold excess of irradiated (40 Gy) allogeneic peripheral blood mononuclear "feeder" cells in complete medium (CM) with 30 ng/ml anti-CD3 antibody and 6000 IU/ml IL-2. Half of the media was exchanged on day 5 using CM with 6000 IU/ml IL-2, and cells were split as needed thereafter. Cell activity was assessed on day 14 of the rapid expansion (TIL expanded an average of more than 3000 fold).

This example demonstrated the generation of "young" tumor-infiltrating lymphocytes (TIL) having an age of 24-32 days.

Example 2

This example demonstrates the testing of young TIL cultures for specific reactivity.

When cultures designated for young TIL generation expanded to confluence in 2-ml wells, they were tested for specific reactivity. Because the young TIL were set up in large numbers (typically groups of 24 per tumor) it was not feasible to count each TIL culture individually. The young TIL specificity assay measures activity per volume rather than activity per cell. Each well was mixed thoroughly, and exactly one hundred microliters of lymphocytes (estimated $1 \times 10^5$ cells) was washed and cocultured with $1 \times 10^5$ autologous or HLA-mismatched tumor cells overnight. IFN-γ release was then measured with enzyme-linked immunosorbent assay (ELISA). A TIL culture was defined as possessing specific reactivity if IFN-γ release was twice background (coculture of TIL with HLA-mismatched tumors) and at least 200 pg/mL unless otherwise noted.

This example demonstrated the testing of young TIL cultures for specific reactivity.

Example 3

This example demonstrates the generation of young lymphocytes for adoptive transfer therapy by growth of TIL from melanoma tumors.

The materials used in this Example include: $Ca^{++}$-, $Mg^{++}$-, Phenol red-free Hanks' balanced salt solution (HBSS) (Bio-Whittaker); RPMI 1640 with L-Glutamine (Bio Whittaker; Walkersville, Md.); AIM-V medium, (GIBCO, Life Technologies; Grand Island, N.Y.); Human serum, type AB (Approved source with appropriate COA); Recombinant human IL-2 ($10^6$ CU/ml, Chiron Corp., Emeryville, Calif.) (Note: 1000 Cetus Units (CU)=6000 International Units (IU)); Collagenase, type IV, 1 g/liter stock enzyme medium (Sigma-Aldrich; St. Louis, Mo.); Hyaluronidase, type V, 100 mg/liter stock enzyme medium (Sigma-Aldrich); Deoxyribonuclease (DNAase), type IV, 30,000 units/liter stock enzyme medium (Sigma-Aldrich); Gentamicin sulfate, 10 mg/ml, stock (Bio-Whittaker) (Omit if patient is allergic to gentamicin); L-Glutamine, 29.2 mg/ml, stock (Mediatech; Herndon, Va.); Penicillin/Streptomycin (10,000 units Pen/ml, 10,000 µg Strep/ml) (BioWhittaker) (Omit if patient is allergic to penicillin/streptomycin); OKT3 (Ortho-anti-CD3) (Orthoclone); Fungizone, 250 µg/ml, stock (Bristol-Myers Squibb Co.; Princeton, N.J.) (Omit if patient is allergic to fungizone); Ciprofloxacin, 10 mg/ml stock, (Bayer, West Haven, Conn.) (Omit if patient is allergic to ciprofloxacin); Lymphocyte separation medium (LSM), (ICN Biomed, Inc; Avrora, Ohio); Albumin (Human) 25%, USP, (100 ml, Baxter Healthcare Co.; Glendale, Calif.); Nalge filters; 0.8, 0.45, and 0.22 µm (1 package of each; Nalge Company, A Subsidiary of Sybron, Rochester, N.Y.); Sterile water for injection, USP (10 ml; American Pharmaceutical Partners, Inc.; Los Angeles, Calif.); Dissecting board, sterile; Sterile scalpels, forceps, and scissors, at least 2 of each; Magnetic stir bar, sterile; Receiving units, sterile (250-500 ml sizes, Nalge Company, A Subsidiary of Sybron, Rochester, N.Y.); Funnel and metal mesh filters, sterile; Centrifuge tubes, 50 ml and 250 ml; Plastic pipets, sterile 10, 25 and 50 ml; Tissue culture plates, sterile 24 and 6 well; Tissue culture flasks, 175 $cm^2$; Syringes, 1, 12 and 60 ml; Needles, 19 and 25 gauge; Sampling site coupler, (Baxter/Fenwal, Deerfield, Ill.); Solution transfer set, (Baxter/Fenwal, Deerfield, Ill.); Lifecell adapter set, (Baxter/Fenwal, Deerfield, Ill.); Interconnecting jumper tube, 8" (GIBCO, Life Technologies; Grand Island, N.Y.); Solution transfer pump; (Baxter/Fenwal, Deerfield, Ill.); Culture bags, PL732 1 liter (Baxter/Fenwal, Deerfield, Ill.); Culture bags, PL732 3 liter (Baxter/Fenwal, Deerfield, Ill.). Centrifugation g forces relate to the bottom of the centrifuge tube in a Sorvall RC-3B centrifuge: 2000 rpm~1100×g; 1500 rpm~600×g; 800 rpm~175×g.

Enzyme Preparation for Dispersing Tumor Cells.

Enzyme-containing medium is used to disperse tumor cells from the surgical specimen. It is filtered through a 0.22 µm filter before use and can be stored at 4° C. for up to 3 months in a sealed container. The enzyme-containing medium, RPMI 1640, does not have serum. It has the following added components (final concentrations): antibiotics are penicillin G (50 units/ml), Gentamicin (10 µg/ml), and Amphotericin B (1.25 µg/ml). Add the Amphotericin B after filtering the medium. The medium contains the following final concentrations of enzymes: DNAse (30 units/ml), hyaluronidase (100 µg/ml), and collagenase (1 mg/ml). The enzyme stocks are dry powders that are stored at −20° C.

Media.

Prepare complete medium (CM) for culturing TIL by supplementing RPMI-1640 with 10% human serum (Approved source, heat-inactivated 56° C. for 30 minutes), and also with final concentrations of penicillin G (100 units/ml), streptomycin (100 µg/ml), gentamicin (50 µg/ml), L-glutamine (146 µg/ml, 1 mM). Omit selected antibiotics for relevant allergies. Other GMP quality media additives may be used when necessary (e.g. imipenem). Filter CM through a 0.22 µm filter before use. Store at 4° C. and use within a week.

Dispersing Cells from Tumor Explants

On the day of tumor resection, receive the specimen in the laboratory as soon as possible after surgery. Transport the resected tissue bathed in sterile saline in a sterile container. Once the specimen arrives in the laboratory, perform all processing procedures in a laminar flow biological safety cabinet.

Place the tissue specimen on a sterile dissecting board with all dissecting instruments (scalpels, scissors, forceps etc.) easily within reach. The pathologist covering TIL tumor samples should be present before the tissue sample is processed. Assess the extent of tumor in the specimen. Measure the tissue dimensions using the scale in the dissection board and help the pathologist make observations needed for their report. Once the sampling needs of the pathologist have been met and the tumor mass has been isolated, there are several options for the initial cell preparation for culturing tumor infiltrating lymphocytes: a fine needle aspirate from the tumor tissue; tumor fragments, cut with a scalpel or scissors to ~1-1.5 mm in each of 3 dimensions; a mechanically dispersed, single-cell suspension; and an enzymatically generated single-cell suspension.

Irrespective of the source, or sources, of the starting material, initiate the cell expansions in 24-well plates in culture media containing 1000 CU/ml IL-2. When using tumor fragments, start with one fragment per well. Keep tumor fragments bathed in HBSS while they are on the cutting board; otherwise they will dry out quickly. To prepare a single-cell suspension mechanically, use the BD™ Medimachine System (Becton Dickinson; San Jose, Calif.).

The following description applies to enzymatically generated single cell suspensions, but the principles are broadly applicable. Mince each tumor slice into 1-3 $mm^3$ chunks using either cross scalpel cuts or cutting with scissors. Transfer up to about 30 mls of the tumor chunks with a sterile plastic spoon to a sterile container with about 100 ml of enzyme-containing medium (collagenase, hyaluronidase and DNAase). The volume of medium should be scaled up in a linear fashion for larger amounts of tumor. Cap the container tightly and place it on a magnetic stirrer. Stir the tumor chunks gently overnight (18-24 hours) at room temperature. Many tumors, such as melanomas, are completely digested in 2-6 hours. However, the more fibrotic tumors require overnight digestion. In either case, the overnight digestion does not appear to hurt the final viability of the lymphocytes in the single cell suspension. If time does not allow for an overnight digestion, tumors can be digested for several hours at 37° C. until the cell dispersion is adequate. Also, if the overnight digestion is incomplete, an additional few hours of incubation at 37° C. may help.

After the tumor digestion is finished, filter the cell suspension through a sterile metal mesh filter (held in a sterile plastic funnel) into 250 ml capacity sterile centrifuge tubes. The filter is designed to remove residual tumor and connective tissue. Add HBSS ($Ca^{++}$, $Mg^{++}$-free) from a fresh bottle, to the single cell suspension to top off the centrifuge tube. Then centrifuge the single cell suspension at 1100 rpm (~400×g) for 15 minutes. Following centrifugation, aspirate the supernatant, resuspend the pellet in fresh HBSS, and repeat the wash process for a total of 3 times (the first spin counting as wash number 1).

Combine the cell pellets, resuspended in HBSS, in a single tube, and determine the total viable nucleated cell number. For records, distinguish between live tumor cells, live lymphoid cells, dead cells and erythrocytes. Nuclei and other subcellular particles are not counted. In general, cell viability by trypan blue exclusion is 60% or greater, and the RBCs are less than 10× in excess of viable nucleated cells. Otherwise, the viable nucleated cells may be enriched by using a Ficoll-Hypaque gradient. Although Ficoll-Hypaque (LSM) was designed to separate mononuclear cells from erythrocytes in peripheral blood, it is often useful in cleaning up tumor specimens and separating dead cells and erythrocytes from viable tumor and host lymphocytes.

All viable cells that are prepared from a patient's tumor may be set up for TIL cultures, or, if the yield is this high, samples may be processed for cryopreservation. Typically, $8 \times 10^6$ to $4 \times 10^8$ viable cells will be initiated as the TIL culture. Alternatively, $4 \times 10^6$ enzymatically dispersed cells (four wells) are cultured for TIL cultures when TIL from tumor fragments (typically ~8 wells) are also cultured. Enzymatically dispersed cells may also be used to start tumor or fibroblast cell lines, but it is believed that greater success is achieved when generating tumor lines from mechanically dispersed cells. The remaining cells may be cryopreserved in vials ($2 \times 10^7$ cells per vial are commonly used).

In cases where Ficoll-Hypaque gradients are needed, gradients are established by underlaying 40 ml of the single cell suspension with 10 ml of LSM. Determine the number of gradients by the packed cell volume. Use about 0.5-1.0 ml packed cells to each 50 ml FH gradient. Following centrifugation (2,000 rpm (~1100×g)×15 minutes), remove the buffy coats, consolidate them in an appropriate number of 50 or 250 ml tubes, and wash 3 times using $Ca^{++}$-, $Mg^{++}$-free HBSS. For washing large tumor preps, pool the bands from 5 gradients in a single 250 ml conical. For the first wash, add at least an equal volume of Hanks to the cell suspension and centrifuge at 2,000 rpm for 10 minutes. The remaining centrifugations are at 1,500 rpm (~600×g) for 10 minutes. After the final wash, assess the cell pellet for total viable cell number using trypan blue exclusion. For melanoma tumors, mononuclear cells can often be distinguished from tumor cells by cell size and morphology.

Bulk TIL Cultures

TIL cultures are set up in 24-well sterile tissue culture plates, using $5.0 \times 10^5$ total viable nucleated cells (e.g., lymphocytes, tumor cells, macrophages, fibroblasts)/ml ($1.0 \times 10^6$ total viable cells/well, 2 ml/well) of complete culture medium containing 1000 CU/ml IL-2. The plates are incubated in a humidified incubator at 37° C., with 5% $CO_2$ in air.

After about one week, the TIL cultures should be assessed for growth using trypan blue staining and counting of viable cells, and the wells should be viewed under a high quality inverted phase microscope. If lymphocytes are not confluent, or the TIL have not expanded to a level of $1.5 \times 10^6$ TIL (lymphocytes)/ml or greater, then half of the CM is replaced with fresh medium containing IL-2 (1000 CU/ml). This is accomplished by removing one ml media by aspiration, taking care not to disturb the cells on the bottom of the well, and replacing it by adding 1 ml fresh medium containing IL-2 (1000 CU/ml). This should be repeated three times per week until the culture exceeds $5 \times 10^6$ lymphocytes/ml or becomes nearly confluent. If the TIL are not growing by 2 weeks or their concentration is under $5 \times 10^5$/ml and/or cell viability is under 60%, consider concentrating the cells and/or enriching the viable cells by Ficoll-Hypaque separation.

When the TIL have grown to $1.5 \times 10^6$/ml or greater, or if lymphocytes are confluent throughout the wells, the individual culture wells should be pooled. Aliquots may be cryopreserved immediately or the cells may be expanded further by re-plating at $0.7-1.5 \times 10^6$ lymphocytes/ml in CM containing IL-2 (1000 CU/ml) until sufficient cells are obtained. An aliquot of bulk TIL will be examined by FACS to determine the percentage of CD8+ cells. The results of this analysis will be used to determine the starting TIL cell number and the volume of anti-CD8 beads to be used in the subsequent CD8 selection protocol steps.

Sufficient bulk TIL will be pooled for an estimated CD8+ cell yield after selection of $>30 \times 10^6$ cells. Bulk TIL cells will be subjected to the CD8+ positive selection process as detailed in Example 9.

In process validation testing will include viable cell counting and FACS analysis of the following samples 1) the starting bulk TIL population 2) the "flow through" depleted population and 3) the CD8+ selected population. The resulting CD8+ selected fraction will be used as the responding cell population in clinical scale REP (see below) and will constitute the product administered to the patient.

Clinical Scale Rapid Expansion

Each lymphocyte culture is expanded using a single Rapid Expansion Protocol (REP). During the expansion procedure, tests for efficacy and safety are performed as set forth in Table 3, and the cells are prepared for patient infusion after about 14 days from REP initiation.

TABLE 3

| Test | Method | Limits |
|---|---|---|
| Cell viability[1] | trypan blue exclusion | >70% |
| Total viable cell number[1] | visual microscopic count | $>5 \times 10^8$ |
| TIL potency[2] | OKT3-stimulated IFN release | >200 pg/ml per $10^5$ cells |
| Microbiological studies | gram stain[1,3] | no micro-organisms seen |
| | aerobic culture[3,4] | no growth |
| | fungal culture[3,4] | no growth |
| | anaerobic culture[3,4] | no growth |
| | mycoplasma test[2] | negative |
| Endotoxin[1] | limulus assay | #5 E.U./kg |
| Presence of tumor cells[2] | Cytopathology | No tumor cells per 200 cells examined |

[1]Performed on the final product prior to infusion. Results are available at the time of infusion.
[2]Performed 2-10 days prior to infusion (test performed prior to final manipulation). Results are available at the time of infusion.
[3]Performed 2-4 days prior to infusion. Results are available at the time of infusion but may not be definitive.
[4]Sample for test collected on the final product prior to infusion. Results will not be available before cells are infused into the patient.

TIL are washed by centrifugation at 600×g, resuspended in CM, counted, and viable cells are added to the other components in proportions indicated in Table 4. Fungizone and Ciprofloxacin are added to all growth media starting on day 7.

TABLE 4

| Component | 175 cm² flask | 6 × 175 cm² flask | Aastrom Replicel |
|---|---|---|---|
| viable TIL | $1 \times 10^6$ | $6 \times 10^6$ | $5\text{-}10 \times 10^6$ |
| feeder PBMC* | $2 \times 10^8$ | $1.2 \times 10^9$ | $1.0 \times 10^9$ |
| OKT3 | 30 ng/ml | 30 ng/ml | 30 ng/ml |
| rhIL-2 | 1000 CU/ml | 1000 CU/ml | 1000 CU/ml |
| CM | 75 ml | 450 ml | 100 ml |
| AIM V | 75 ml | 450 ml | 100 ml |

*On the day that the REP is set up, previously pedigreed and cryopreserved feeder PBMC are thawed, or fresh feeder cells are prepared by Ficoll-Hypaque gradient from a lymphocytapheresis. The cells are washed by centrifugation and resuspended in CM. Feeder cells can consist of autologous PBMC or allogeneic PBMC that have been certified to pass all criteria in Table 3. Feeder cells are irradiated (40 Gy) prior to use, and radiation is carefully annotated prior to adding feeders to other REP components. PBMC, IL-2, and OKT3 are added to CM and AIM V, mixed well. Viable cells are then added and aliquots are transferred to tissue culture flasks. Flasks are incubated upright at 37° C. in 5% $CO_2$.

On the fifth day after initiating the REP (day 5), 120 ml is aspirated from each a 175 cm² flask (cells are retained on the bottom of the flask). Media is replaced with CM/AIM V 50/50 containing 1000 CU/ml IL-2.

On days 7 or 8 the cells are transferred to bags (two flasks per 3 liter PL732 bag) and fed by the addition of an equal volume (300 ml) AIM V media supplemented with 5% human serum, 1000 CU/ml IL-2, Fungizone (1.25 mcg/ml) and Cipro (1 ml/l). The AIM-V being added to the 3 liter PL732 bag is transferred with a Baxter solution transfer pump from a 10 liter STAK PACK of AIM-V medium (GIBCO; Life Technologies, Grand Island, N.Y.) using a sterile solution transfer set, a Life-adapter set, and an 8" (20.32 cm) interconnecting jumper tube.

On days 8 through harvest, the expanding cultures are maintained at a cell density of 0.8–2.0×10$^6$ cells per ml by the addition of Aim V media containing 1000 CU/ml IL-2, Fungizone and Cipro. TIL cultures are commonly split to new bags containing fresh medium on day 10-12. In general, REPs of bulk TIL cultures results in 500-2000 fold expansions. At any time during cell expansion, cell aliquots may be removed and assayed for quality assurance and/or sterility tests as required by the certificate of analysis for infused cell products. If cells have grown to sufficient numbers for patient treatment, a sample is collected from representative bags or flasks for microbiology tests 2-3 days before the cells are harvested for infusion.

Preparation of Cells for Infusion

Check the quality control tests in Table 3 that are needed before infusion of the cells. The product for infusion is prepared by harvesting and washing the cells in centrifuge tubes or in a continuous centrifuge cell harvester system. Cell cultures in flasks or a small number of Nexell culture bags are transferred to 250 ml centrifuge tubes. These cells are centrifuged (400×g for 15 min), and then resuspended in HBSS and combined in a single 250 ml tube. With about 4 liters or more of culture fluid in Nexell culture bags, the cells are harvested with the Baxter/Fenwall harvester system, the last step of which is a 2-liter wash with 0.9% sodium chloride. Cells from the continuous centrifuge harvest are transferred from the harvest bag to 250 ml centrifuge tubes. For the last step of both harvesting procedures, cells are centrifuged and resuspended in 100-400 ml of 0.9% sodium chloride containing 1) human albumin (25%) added to a final concentration of 2.5% and 2) recombinant human IL-2 at a final concentration of 50 CU/ml. The cell suspension is then transferred into the infusion bag. The range of cells in the infusion bag is specified in the clinical protocol. Aliquots are taken from the infusion bag for viable cell counting, quality control testing, and cryopreservation of cells. The product is then transferred to the clinical team for infusion as soon as possible.

This example demonstrated the generation of young lymphocyte cultures for adoptive transfer therapy by growth of TIL from melanoma tumors.

Example 4

This example demonstrates that tumor reactive cells are detected at equal frequencies in young TIL cultures and standard TIL cultures generated from TIL fragments.

The kinetics of the development of tumor reactivity in TIL cultures was investigated by testing individual cultures derived from a single tumor for activity and specificity at two times during culture progression. TIL were initially tested at the earliest time after all tumor cells were lysed, when lymphocytes had recently become confluent in their initial wells. TIL cultures were tested a second time approximately 13 days later after each culture had been passaged and expanded extensively in vitro. Eighteen of 34 consecutive tumor specimens received in the Cell Processing Facility were sufficiently large to establish both young TIL and standard TIL cultures from dissected tumor fragments (Table 5).

TABLE 5

| | Young | | | Standard | | |
|---|---|---|---|---|---|---|
| Specimen ID* | Setup† | Reactive (%)‡ | Age§ | Setup | Reactive (%) | Age |
| 4 | 12 | 10 (83) | 12 | 3 | 1 (33) | 27 |
| 5 | 24 | 21 (88) | 17 | 3 | 3 (100) | 26 |
| 6 | 28 | 27 (96) | 14 | 3 | 3 (100) | 25 |
| 8 | 24 | 0 (0) | 10 | 8 | 5 (63) | 27 |
| 9 | 32 | 32 (100) | 7 | 8 | 8 (100) | 14 |
| 10 | 24 | 1 (4) | 18 | 8 | 0 (0) | NG¶ |
| 13 | 16 | 2 (13) | 10 | 8 | 0 (0) | 21 |
| 16 | 24 | 0 (0) | 17 | 8 | 0 (0) | 33 |
| 18 | 16 | 0 (0) | 14 | 8 | 0 (0) | 28 |
| 22 | 12 | 0 (0) | 7 | 8 | 1 (13) | 21 |
| 23 | 12 | 9 (75) | 7 | 8 | 0 (0) | 27 |
| 24 | 8 | 2 (25) | 14 | 2 | 2 (100) | 20 |
| 25 | 12 | 0 (0) | 12 | 8 | 0 (0) | 27 |
| 34 | 12 | 12 (100) | 12 | 16 | 12 (75) | 26 |
| Mean age | | | 12 | | | 25 |
| Total positive (%)\\ | | 7 (39) | | | 7 (39) | |

*Eighteen out of 34 consecutive specimens had tumor fragments that were used to generate young and standard TIL. Four specimens did not expand and are not listed.
†Number of fragments set up for TIL from each tumor specimen.
‡Number (and percent) of TIL which expanded and had specific reactivity. Specimens which had 25% or more TIL cultures with specific reactivity as defined by at least 200 pg/mL and greater than twice IFN-γ released by coculture with HLA-mismatched controls were considered positive (bold).
§Age (days) at which TIL were tested for reactivity.
¶TIL did not expand adequately for screening.
\\Total number and frequency of positive specimens for all 18 specimens.

Specificity testing by IFN-γ release assay demonstrated that seven young TIL from fragments had specific reactivity (39%) and seven standard TIL from fragments also had specific reactivity (39%). Six tumor specimens (33%) had specific reactivity for both young and standard TIL. At the time of testing for specificity, young TIL had a mean age of 12 days and standard TIL had a mean age of 25 days.

Sixteen out of 34 consecutive tumors had enough tissue to generate both standard and young TIL by the enzymatic digestion method (Table 6).

TABLE 6

| Specimen ID* | Young | | | Standard | | |
|---|---|---|---|---|---|---|
| | Setup† | Reactive(%)‡ | Age§ | Setup | Reactive(%) | Age |
| 1 | 96 | 18(19) | 14 | 4 | 0(0) | NG¶ |
| 5 | 96 | 72(75) | 17 | 3 | 3(100) | 26 |
| 6 | 24 | 19(79) | 16 | 3 | 3(100) | 24 |
| 8 | 24 | 0(0) | 9 | 4 | 0(0) | 46 |
| 9 | 48 | 41(85) | 9 | 4 | 0(0) | NG |
| 10 | 48 | 1(2) | 11 | 4 | 0(0) | 25 |
| 16 | 48 | 0(0) | 16 | 4 | 0(0) | NG |
| 18 | 48 | 0(0) | 13 | 4 | 2(50) | 27 |
| 22 | 24 | 13(54) | 13 | 4 | 0(0) | 20 |
| 23 | 24 | 15(63) | 13 | 4 | 2(50) | 26 |
| 24 | 48 | 48(100) | 13 | 4 | 2(50) | 19 |
| 32 | 24 | 24(100) | 12 | 4 | 4(100) | 24 |
| Mean age | | | 13 | | | 26 |
| Total positive (%)\\ | | 7(44) | | | 6(38) | |

*Sixteen out of consecutive 34 specimens had enzymatic digests that were used to generate young and standard TIL. Four specimens did not expand and are not listed.
†Number of single-cell suspensions set up for TIL from each tumor specimen.
‡Number and percent of TIL which expanded and had specific reactivity. Specimens which had 25% or more TIL cultures with specific reactivity as defined by at least 200 pg/mL and greater than twice IFN-γ released by coculture with HLA-mismatched controls were considered positive (bold).
§Age (days) at which TIL were tested for reactivity.
¶TIL did not expand adequately for screening.
\\Total number and frequency of positive specimens for all 16 specimens.

The same trend of reactivity observed for tumor fragments was seen for enzymatic digests of tumor. Testing by IFN-γ release assay demonstrated that seven young TIL (44%) had specific reactivity and six standard TIL (38%) had specific reactivity. Five specimens (31%) had specific reactivity for both young and standard TIL.

This example demonstrated that tumor reactive cells are detected at equal frequencies in young TIL cultures and standard TIL cultures generated from TIL fragments.

Example 5

This example demonstrates that the tumor reactivity of young TIL is maintained during in vitro expansion.

To test the stability of the tumor recognition during large numerical expansions, four young TIL with autologous tumor reactivity (Table 7) were identified.

The TIL were expanded to approximately $2 \times 10^6$ cells (as demonstrated by confluent growth in 2-ml culture wells) at which time the mean age of these TIL was 12 days. The cells were harvested and tested for reactivity by IFN ELISA. Portions of each TIL culture were further expanded with IL-2 alone (comparable to the currently used standard method) or rapidly expanded with IL-2, OKT3, and feeder cells for 14 more days. Thus the 12-day old TIL represent young TIL prior to REP, the TIL which underwent additional standard expansion represent standard TIL prior to REP (mean age=26 days), and the TIL which underwent rapid expansion represent young TIL after REP (mean age=26 days). All TIL were then tested for specific reactivity to autologous tumor in a single ELISA assay. The cultures that were expanded as standard TIL exhibited an average of 19 fold growth over the 14 day assay period. Three of the four cultures retained specific recognition of autologous tumor after standard expansion. The rapidly expanded TIL increased in number by an average of 3116 fold over the same 14-day period. The three TIL cultures which showed specificity with standard expansion also demonstrated specificity after rapid expansion (Table 7).

TABLE 7

| | Young TIL* | | Standard Expansion† | | | Rapid Expansion‡ | | |
|---|---|---|---|---|---|---|---|---|
| Specimen | Autol§ | Contr¶ | Autol | Contr | Exp | Autol | Contr | Exp |
| 1 | 381 | 31 | 1448 | 111 | 30 | 1634 | 650 | 4166 |
| 2 | 565 | 107 | 983 | 160 | 31 | 1053 | 523 | 3744 |
| 3 | 103 | 0 | 201 | 33 | 12 | 1599 | 513 | 2822 |
| 4 | 691 | 116 | 96 | 52 | 3 | 424 | 1021 | 1733 |

*TIL generated from four enzymatically digested tumor samples were tested for specific reactivity when each culture expanded to $2 \times 10^6$ lymphocytes (mean = 12 days).
†Young TIL were expanded using standard methods for 14 more days and then tested.
‡Young TIL were rapidly expanded for 14 more days and tested.
§Values indicate IFN-γ release (pg/mL) when cocultured with autologous tumor. Bold numbers indicate a tumor-specific reactive test defined as at least 100 pg/mL and greater than twice IFN-γ released by coculture with HLA-mismatched controls.
¶Values indicate IFN-γ release (pg/mL) when cocultured with HLA-mismatched control tumors.

As shown in Table 7, TIL demonstrating specific reactivity at a young age usually maintain reactivity after both standard expansion and rapid expansion, and supports the use of young TIL instead of standard TIL for adoptive transfer.

This example demonstrated that the tumor reactivity of young TIL is maintained during in vitro expansion.

Example 6

This example demonstrates that young TIL have a higher frequency of CD4+ cells than standard TIL.

Figure 1:
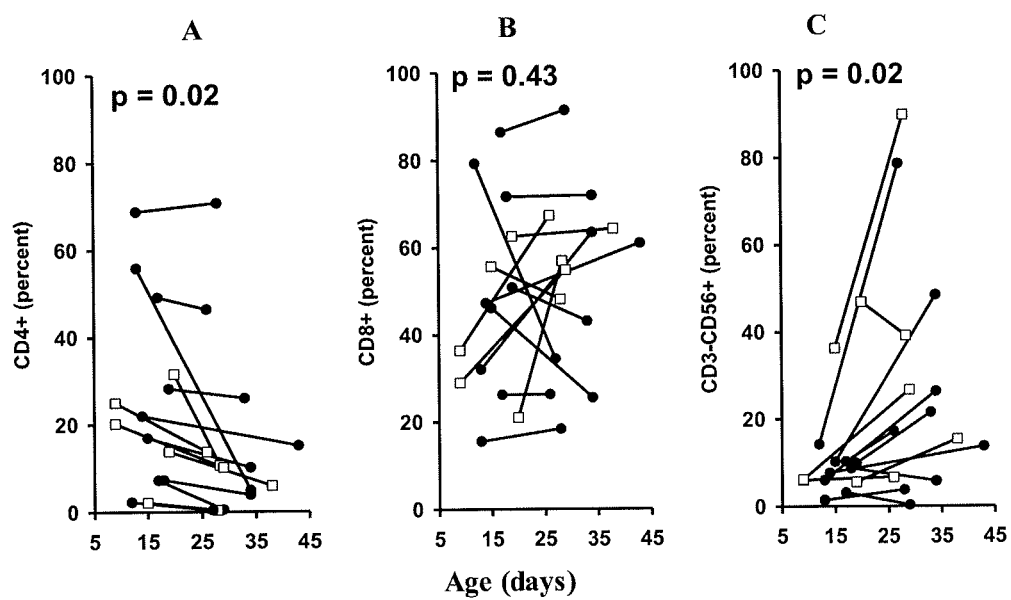
FIG. 1A is a graph showing the frequency (percent) CD4+ marker expression (y axis) per days in culture (x axis) for tumor infiltrating lymphocytes (TIL) generated from enzymatic digests of tumor (filled circles) and TIL from tumor fragments (open squares) (p=0.02).
FIG. 1B is a graph showing the frequency (percent) CD8+ marker expression (y axis) per days in culture (x axis) for TIL generated from enzymatic digests of tumor (filled circles) and TIL from tumor fragments (open squares) (p=0.43).
FIG. 1C is a graph showing the frequency (percent) CD3-CD56+ marker expression (y axis) per days in culture (x axis) for TIL generated from enzymatic digests of tumor (filled circles) and TIL from tumor fragments (open squares) (p=0.02).

To investigate the cellular composition of TIL cultures over time, aliquots of 14 TIL cultures were sampled and cryopreserved as soon as the lymphocytes became confluent and tumor cells were eliminated from wells. Then cultures were maintained by standard methods for 14 additional days and another sample was cryopreserved. Then both samples were thawed and analyzed by FACS simultaneously. The mean age was 15 days for young TIL and 31 days for standard TIL. Analysis of lymphocyte subsets in the TIL demonstrated that the young TIL had a higher frequency of $CD4^+$ lymphocytes than standard TIL (FIG. 1A, p=0.02). However, there were no significant differences in the frequency of $CD8^+$ cells between young and standard TIL (FIG. 1B). The frequency of CD3-$CD56^+$ natural killer (NK) cells was lower in young TIL (p=0.02, FIG. 1C).

This example demonstrated that young TIL have a higher frequency of CD4+ cells than standard TIL.

Example 7

This example demonstrates that young TIL express higher levels of costimulatory molecules than standard TIL.

Figure 2:
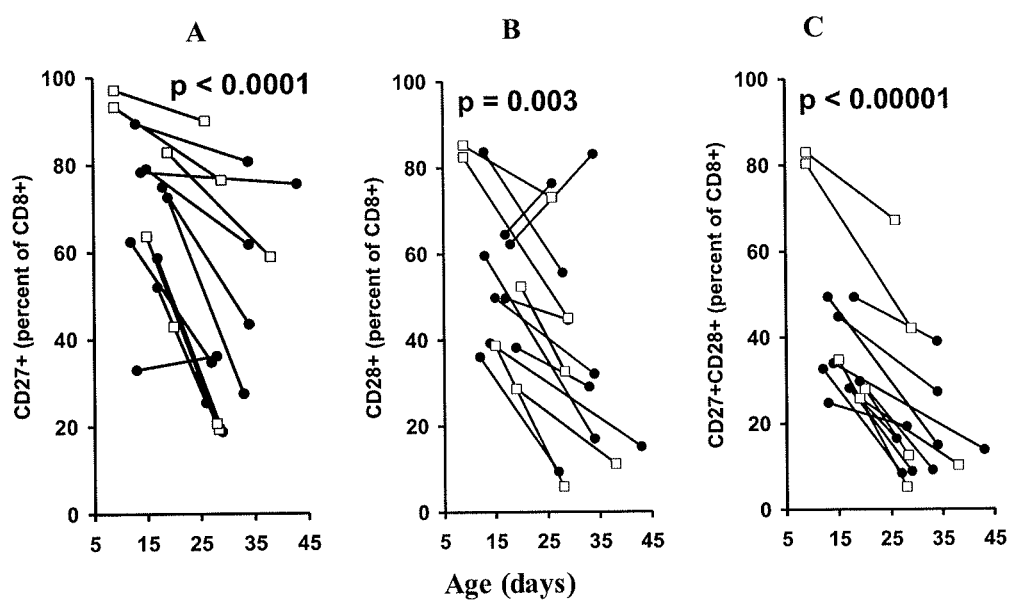
FIG. 2A is a graph showing the frequency (percent) CD27+ marker expression of CD8+ cells (y axis) per days in culture (x axis) for TIL generated from enzymatic digests of tumor (filled circles) and TIL from tumor fragments (open squares) (p<0.0001).
FIG. 2B is a graph showing the frequency (percent) CD28+ marker expression of CD8+ cells (y axis) per days in culture (x axis) for TIL generated from enzymatic digests of tumor (filled circles) and TIL from tumor fragments (open squares) (p=0.003).
FIG. 2C is a graph showing the frequency (percent) CD27+ CD28+ marker expression of CD8+ cells (y axis) per days in culture (x axis) for TIL generated from enzymatic digests of tumor (filled circles) and TIL from tumor fragments (open squares) (p<0.00001).

FACS analysis of gated CD8+ cells from the TIL populations generated in Example 6 demonstrated a strong relationship between culture age and the expression of CD27 and CD28 (FIGS. 2A, 2B, and 2C). Strikingly, the percentage of CD8+ cells co-expressing CD27 and CD28 was higher in all 14 samples of younger TIL than standard TIL. There were no significant differences in the expression of CD62L and CCR7 by young and standard TIL (data not shown).

This example demonstrated that young TIL express higher levels of costimulatory molecules than standard TIL.

Example 8

This example demonstrates that young TIL have longer telomeres than standard TIL.

Figure 3:
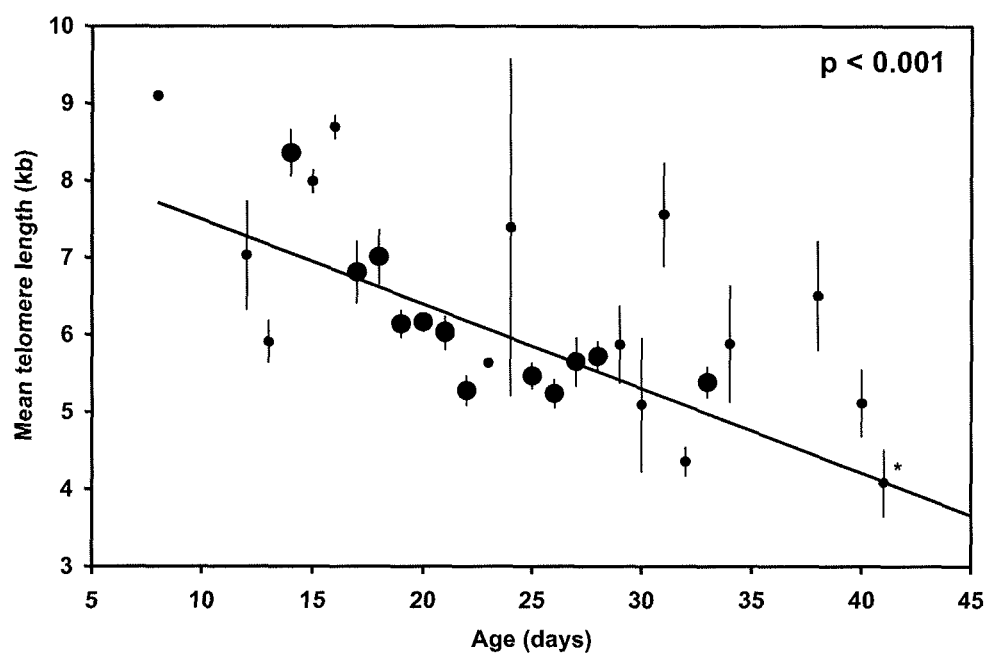
FIG. 3 is a graph showing mean telomere length (kb) (y axis) for TIL cultured per days in culture (x axis) (p<0.001).

To investigate the impact of culture time on the telomere lengths of the TIL, 495 independent TIL cultures from 48 consecutive specimens were tested. Telomere lengths of 495 TIL from 48 consecutive patients were evaluated by quantitative fluorescent in-situ hybridization. As shown in FIG. 3, although the telomere lengths varied widely at any given TIL age, there was an inverse correlation between time in culture and the mean telomere length of TIL ($p<0.001$).

This example demonstrated that young TIL have longer telomeres than standard TIL.

Example 9

This example demonstrates the enrichment of cultured T cells for CD8+ cells.

The materials used in this Example include: Peripheral Blood Lymphocyte (PBL) product containing up to $40\times10^9$ total cells and up to $4\times10^9$ CD8+ cells; CliniMACS CD8 MicroBeads; CliniMACS$^{plus}$ Instrument, Miltenyi Biotec (e.g., Order No. 155-02), software version 2.3×; 1 CliniMACS Tubing Set, Miltenyi Biotec (e.g., Order No. 165-01), or 1 CliniMACS LS Tubing Set, Miltenyi Biotec (e.g., Order No. 168-01); 1 Pre-System Filter, Miltenyi Biotec, Order No. 181-01; 1 Luer/Spike Interconnector, Miltenyi Biotec, Order No. 187-01; CliniMACS PBS/EDTA buffer, Miltenyi Biotec (e.g., Order No. 705-25); Human Serum Albumine (HSA) supplement to CliniMACS PBS/EDTA buffer, final concentration 0.5%; 250 ml centrifuge tubes; Immune Globulin Intravenous (Human), 10% (GAMMAGARD LIQUID, Baxter); Transfer Bags 600 ml, Miltenyi Biotec, Order No. 190-01; Digital Balance; Sterile Tubing Welder; Orbital Shaker; Sampling Site Coupler; Tubing Slide Clamps or Scissor clamps. CliniMACS CD8 MicroBeads are manufactured under an ISO 9001 certified Quality System and follows cGMP guidelines.

A typical pheresis product was obtained and processed (starting cells). $3.88\times10^9$ peripheral blood mononuclear cells were applied to the CliniMACS$^{plus}$ and Enrichment 1.1 program using tubing set 165-01, Process CODE: 0211020F0000834.

The positive selection of CD8 positive T cells is performed by immunomagnetic labeling of CD8 expressing cells and enrichment of these cells from the target fraction by automatic cell separation using the CliniMACS$^{plus}$ Instrument. The highly purified CD8+ cells are collected in the Cell Collection Bag.

The content of one vial of CliniMACS CD8 MicroBeads is sufficient for labeling of up to $4\times10^9$ CD8 positive cells out of a total leukocyte number of up to $40\times10^9$ cells (normal scale preparation (A). For processing of 2 to $4\times10^9$ CD8 positive cells or 20 to $40\times10^9$ leukocytes two CliniMACS CD8 MicroBeads vials are needed to achieve sufficient labelling (large scale preparation (B)). Weigh the empty Cell Preparation tube prior to transferring the PBL into the Cell Preparation tube. Determine the volume of the PBL by weighing the filled Cell Preparation tube and subtracting the empty tube weight. Use a small aliquot of the PBL to determine the total number of leukocytes and the viability. When process timing allows, use FACS analysis to determine the percentage of target cells. If process timing is insufficient for FACS analysis, assume a CD8+ percentage of 20% of the total pheresis product.

Dilute the PBL (1:3) with CliniMACS PBS/EDTA Buffer (supplemented with 0.5% HSA) and centrifuge the cells at 300×g for 10 minutes. Calculate the amount of buffer to be added using the following equation: Weight of buffer to be added (g)=Weight of PBL (g)×2. Spin down the cells (300×g, 10 min, room temperature (+19° C. to +25° C.)). Remove the supernatant and adjust the sample to a labeling volume of A) 400 mL (normal scale) and distribute evenly to two 250 ml tubes. Add 1.25 ml Gammagard per tube (2.5 ml total). Mix gently. Add 1.0 ml CliniMACS CD8 MicroBeads to each tube and mix carefully.

Incubate the cell preparation tubes for 30 minutes at controlled room temperature (+19° C. to +25° C.) on an orbital shaker at 25 rpm. After 30 minutes rocking, spin down the cells for 15 minutes at room temperature and 300×g. Remove as much supernatant as possible from the Cell Preparation tubes and resuspend the cells in CliniMACS buffer. Combine the cell pellets into one tube. Adjust the cell concentration after the washing step to $0.4\times10^9$ total cells/mL. The final sampling volume of the PBL for loading on the CliniMACS$^{plus}$ Instrument should not exceed 275 mL.

Transfer a 0.5 mL sample to a sample tube for flow cytometric analysis. It is recommended to determine at least the cell concentration, the viability, and the frequency/number of the target cells.

Automated Separation

Switch on the CliniMACS$^{plus}$ Instrument and select a suitable program: positive selection of cells, ENRICHMENT 1.1 is recommended.

Confirm your choice by pressing "ENT" and select a tubing set. CliniMACS Tubing Sets are available with different tubing and column geometry. They differ, e.g., in the maximum cell capacity that can be processed. For further information refer to the CliniMACS$^{plus}$ User Manual "General Instructions." Enter the Order No. of the selected tubing set. Selection program ENRICHMENT 1.1, is "staged loading" programs. They include a query for the following parameters to adjust the selection sequence to each individual sample and to provide information on the required buffer and bag volumes: WBC concentration; percentage of labeled cells; total volume of the sample ready for loading on the CliniMACS Tubing Set.

Follow the instructions given on the instrument screen and connect an appropriate bag to the tubing set using a Luer/Spike Interconnector (Order No. 187-01). Ensure that the slide clamp of the Luer/Spike Interconnector is open. If more than 1 L of buffer is needed, connect two buffer bags using a Plasma Transfer Set with two couplers (order No. 186-01). Use the second port of one of the buffer bags for the connection to the tubing set.

Follow the instructions on the instrument screen for the installation of the tubing set and start the automated separation program. To ensure product sterility, all cell preparation and manipulation steps are performed in a laminar flow hood under aseptic conditions, in the same laboratory where the cells will later be transduced and cultured for eventual production of the patient-specific cell therapeutics.

After the separation has been finished, determine the weight of Cell Collection Bag and take a sample for flow cytometry analysis. An additional analysis of non-target fractions (negative and buffer waste fraction) is useful for a further process optimization.

$0.69 \times 10^9$ CD8 enriched cells were recovered and analyzed by FACS analysis (Table 8).

TABLE 8

| CD3+ lymphocytes | Starting cells (%) | CD8 enriched cells (%) |
|---|---|---|
| CD3+ CD4+ | 33.35 | 5.02 |
| CD3+ CD8+ | 44.10 | 88.67 |
| CD3− CD8+ | 5.91 | 10.34 |

This example demonstrated the enrichment of cultured T cells for CD8+ cells.

Example 10

This example demonstrates the transduction efficiency of CD8 enriched cells following CliniMACS$^{plus}$ separation.

Samples from the initial (unseparated) PBMC pheresis product and the CD8+ enriched product obtained in Example 9 were stimulated for two days with OKT3 and IL-2 under optimized conditions.

Samples were transduced with clinical grade MART TCR retroviral supernatant and expanded for four more days. Untransduced controls (NV) were expanded similarly. All cultures expanded at equivalent rates.

Transduction efficiency was determined by FACS analysis for VB12 expression and A2/MART-1 tetramer staining (Table 9).

TABLE 9

|  | Starting cells (%) | | CD8 enriched cells (%) | |
|---|---|---|---|---|
|  | NV control | MART TCR | NV Control | MART TCR |
| MART-1 tetramer staining |  |  |  |  |
| CD8+ MART− | 53.1 | 55.5 | 95.6 | 96.4 |
| CD8+ MART+ | 0.2 | 0.4 | 0.2 | 1.3 |
| TCR VB12 expression |  |  |  |  |
| CD8+ VB12− | 54.0 | 44.6 | 97.5 | 68.2 |
| CD8+ VB12+ | 0.4 | 13.6 | 1.1 | 30.9 |

This example demonstrated the transduction efficiency of CD8 enriched cells following CliniMACS$^{plus}$ separation.

Example 11

This example demonstrates that (i) culturing autologous T cells; (ii) rapidly expanding the cultured T cells; (iii) administering to the mammal nonmyeloablative lymphodepleting chemotherapy; and (iv) after administering nonmyeloablative lymphodepleting chemotherapy, administering to the mammal the expanded T cells, wherein the T cells administered to the mammal are about 19 to about 35 days old, promotes the regression of cancer in human patients.

Objectives.

In cohort 1, to determine the ability of autologous TIL cells infused after minimal in vitro culture in conjunction with high dose aldesleukin (IL-2) following a non-myeloablative lymphodepleting preparative regimen to mediate tumor regression in patients with metastatic melanoma.

In cohort 2, to determine the ability of autologous CD4+ cell depleted TIL cells infused after minimal in vitro culture in conjunction with high dose aldesleukin (IL-2) following a non-myeloablative lymphodepleting preparative regimen to mediate tumor regression in patients with metastatic melanoma.

In cohort 3, to determine the ability of autologous CD4+ cell depleted TIL cells infused after minimal in vitro culture in conjunction with high dose aldesleukin following chemoradiation lymphoid depleting regimen to mediate complete tumor regression in patients with metastatic melanoma.

Evaluate the toxicity of these treatment regimens.

Determine the rate of repopulation of the young TIL cells in treated patients and establish in vitro correlates of TIL cultures that mediate objective response and in vivo persistence.

Design:

Patients will undergo resection to obtain tumor for generation of autologous TIL cultures.

In Cohort 1, all patients will receive a non-myeloablative lymphocyte depleting preparative regimen of cyclophosphamide (60 mg/kg/day IV) on days −7 and −6 and fludarabine (25 mg/m$^2$/day IV) on days −5 through −1. On day 0 patients will receive the infusion of autologous TIL and then begin high-dose aldesleukin (720,000 IU/kg IV every 8 hours for up to 15 doses). Clinical and Immunologic response will be evaluated about 4-6 weeks after TIL infusion.

In Cohort 2, CD4+ cells will be eliminated from the cultures, using the Miltenyi CliniMACS$^{plus}$ apparatus, prior to performing the rapid expansion of the young TIL cells. Patients in cohort 2 will receive CD4+ cell depleted young unselected TIL. Patients will also receive high dose IL-2 after non-myeloablative but lymphodepleting chemotherapy preparative regimen as described above for cohort 1. Clinical and immunologic response will be evaluated about 4-6 weeks after TIL infusion. Using a small optimal two-stage Phase II design, initially 18 patients will be enrolled, and if three or more of the first 18 patients have a clinical response (PR or CR), accrual will continue to 35 patients, targeting a 30% goal for objective response.

In Cohort 3, patients will receive a chemoradiation lymphocyte depleting preparative regimen consisting of cyclophosphamide, fludarabine, and 600 cGy total body irradiation followed by intravenous infusion of autologous CD4+ cell depleted young TIL plus IV high dose IL-2. Clinical and immunologic response will be evaluated about 4-6 weeks after TIL infusion.

Eligibility Assessment and Enrollment 2.1 Eligibility Criteria 2.1.1 Inclusion Criteria Inclusion criteria are set forth in Table 10.

2.1.2 Exclusion Criteria

Exclusion criteria are set forth in Table 10.

TABLE 10

| Inclusion Criteria | Exclusion Criteria |
| --- | --- |
| Measurable metastatic melanoma with at least one lesion that is resectable for TIL generation | Women of child-bearing potential who are pregnant or breastfeeding because of the potentially dangerous effects of the preparative chemotherapy on the fetus or infant. |
| Patients with one or more brain metastases less than 1 cm each, and any patients with 1 or 2 brain metastases greater than 1 cm must have been treated and stable for 3 months | Systemic steroid therapy required. |
| Greater than or equal to 18 years of age | Active systemic infections, coagulation disorders or other active major medical illnesses of the cardiovascular, respiratory or immune system, as evidenced by a positive stress thallium or comparable test, myocardial infarction, cardiac arrhythmias, obstructive or restrictive pulmonary disease. |
| Willing to practice birth control during treatment and for four months after receiving the preparative regimen | Any form of primary immunodeficiency (such as Severe Combined Immunodeficiency Disease and AIDS). |
| Life expectancy of greater than three months | Opportunistic infections (The experimental treatment being evaluated in this protocol depends on an intact immune system. Patients who have decreased immune competence may be less responsive to the experimental treatment and more susceptible to its toxicities.) |
| Willing to sign a durable power of attorney | History of severe immediate hypersensitivity reaction to any of the agents used in this study. |
| Able to understand and sign the Informed Consent Document | History of coronary revascularization or ischemic symptoms |
| Clinical performance status of Eastern Cooperative Oncology Group (ECOG) 0 or 1. | Any patient known to have an LVEF less than or equal to 45%. |
| Hematology: Absolute neutrophil count greater than 1000/mm$^3$ without support of filgrastim Normal white blood cell (WBC) (>3000/mm$^3$). Hemoglobin greater than 8.0 g/dl Platelet count greater than 100,000/mm$^3$ | Documented left ventricular ejection fraction (LVEF) of less than or equal to 45% tested in patients with: Clinically significant atrial and/or ventricular arrhythmias including but not limited to: atrial fibrillation, ventricular tachycardia, second or third degree heart block Age ≥60 years old |
| Serology: Seronegative for human immunodeficiency virus (HIV) antibody. (The experimental treatment being evaluated in this protocol depends on an intact immune system. Patients who are HIV seropositive can have decreased immune competence and thus be less responsive to the experimental treatment and more susceptible to its toxicities.) Seronegative for hepatitis B or hepatitis C. | Documented Forced Expiratory Volume in One Second (FEV1) less than or equal to 60% predicted tested in patients with: A prolonged history of cigarette smoking Symptoms of respiratory dysfunction |
| Chemistry: Serum alanine aminotransferase (ALT)/asparatate aminotransferase (AST) less than three times the upper limit of normal. Serum creatinine less than or equal to 1.6 mg/dl. Total bilirubin less than or equal to 2 mg/dl, except in patients with Gilbert's Syndrome who must have a total bilirubin less than 3 mg/dl. More than four weeks must have elapsed since any prior systemic therapy at the time the patient receives the preparative regimen, and patients' toxicities must have recovered to a grade 1 or less (except for toxicities such as alopecia or vitiligo). Patients may have undergone minor surgical procedures with the past 3 weeks, as long as all toxicities have recovered to grade 1 or less or as specified in the eligibility criteria herein. Six weeks must have elapsed since any prior anti-CTLA4 antibody therapy to allow antibody levels to decline. Patients who have previously received any anti-CTLA4 antibody must have a normal colonoscopy with normal colonic biopsies. | Patients will be excluded from cohort 3 (but eligible for cohort 2), if any of the following conditions occur: Prior radiation which makes the patient ineligible to receive 600 cGy. Inability to mobilize CD34$^+$ cells as described herein. |

2.2 Research Eligibility Evaluation

Within 4 weeks prior to starting the chemotherapy regimen, evaluations will be performed as set forth in Table 11.

TABLE 11

Evaluation

Complete physical examination including height, weight and vital signs and eye exam, noting in detail the exact size and location of any lesions that exist.
Chest x-ray
electrocardiogram (EKG)
Baseline CT of the chest, abdomen and pelvis, and brain magnetic resonance imaging (MRI) to evaluate the status of disease. Additional scans and x-rays may be performed if clinically indicated based on patients' signs and symptoms.
Cardiac Multi Gated Acquisition Scan (MUGA) or echocardiogram, stress thallium) and pulmonary evaluation (PFTs) and colonoscopy.
Note: cardiac evaluation may be performed up to 6 months prior to treatment.
HIV antibody titer and HbsAG determination, anti hepatitis C virus (HCV), anti cytomegalovirus (CMV) antibody titer, herpes simplex virus (HSV) serology, and Epstein-Barr virus (EBV) panel
Verification that HLA typing is completed
For patients in cohort 3 only, 15 mL of clean catch urine to be tested Within 14 days prior to starting the chemotherapy regimen, evaluations will be performed as set forth in Table 12:

TABLE 12

Evaluation

Chem 20 [Sodium (Na), Potassium (K), Chloride (Cl), Total $CO_2$(bicarbonate), Creatinine, Glucose, Urea nitrogen (BUN), Albumin, Calcium total, Magnesium total (Mg), Inorganic Phosphorus, Alkaline Phosphatase, Alanine Aminotransferase/Glutamic-Pyruvic Transaminase (ALT/GPT), Aspartate aminotransferase/Glutamyl oxaloacetic transaminase (AST/GOT), Total Bilirubin, Direct Bilirubin, LD, Total Protein, Total creatine kinase (CK), Uric Acid]and thyroid blood chemistry panel.
complete blood count (CBC), differential, Prothrombin time/partial thromboplastin time (PT/PTT), platelet count
Urinalysis and culture, if indicated Within 7 days prior to starting the chemotherapy regimen, a β-HCG pregnancy test (serum or urine) on all women of child-bearing potential will be performed.

2.3 Patient Registration

Patients will be registered by the clinical fellow or research nurse at the time that they enter the study by faxing a completed eligibility checklist to the Central Registration Office (CRO). Written confirmation of registration to the protocol will be obtained from CRO and placed on the patient's research record.

Study Implementation
Study Design:
3.1.1 Pre-Treatment Phase
3.1.1.1 Autologous Stem Cell Collection (for Cohort 3 only)

Prior to the treatment phase of this study, patients will have stem cells collected and stored for re-infusion after the myeloablation and cell therapy. Patients will receive filgrastim at 8 mcg/kg dose BID (total=16 mcg/kg/day) by subcutaneous injection. The morning dose of filgrastim will be given at approximately 7:00 am each day. Stem cells will be collected by apheresis. Autologous apheresis will start on the fifth day of filgrastim administration, and filgrastim administration and apheresis will be repeated daily for a maximum of 2 days to achieve a sufficient dose of $CD34^+$ cells after ex vivo processing (Miltenyi ClinicMACs). For each daily apheresis a blood volume of 20-35 liters of blood will be processed, using ACD-A anticoagulation, peripheral or central venous access, and calcium replacement as needed, per standard operating procedure of the NIH Clinical Center DTM. Sufficient $CD34^+$ cell doses after Miltenyi Clinic-MACs positive selection are defined as a TARGET of $>4\times10^6$/kg recipient weight, and a minimum of $>2\times10^6$/kg recipient weight. Patients who do not reach the minimum dose of selected $CD34^+$ cells after 2 apheresis collections may be considered for a second cycle of filgrastim mobilization and apheresis collections or may be considered for bone marrow harvest.

If the minimum dose of $CD34^+$ cells has not been reached after 2 cycles of mobilization and collection and/or bone marrow harvest, the patient will be treated in cohort 2.

$CD34^+$ cells will be processed and cryopreserved according to DTM policy and procedure until needed for cell infusion.

3.1.1.2 Cell Preparation (for All Cohorts)

Treatment will be similar to that in approved protocol 99-C-0158/T99-0078: Treatment of Patients with Metastatic Melanoma using Cloned Lymphocytes Following Administration of a Nonmyeloablative but Lymphocyte Depleting Regimen. Patients with metastatic melanoma will have TIL obtained while enrolled on the Surgery Branch protocol 03-C-0277, "Cell Harvest and Preparation for Surgery Branch Adoptive Cell Therapy Protocols". Separate tumor biopsies may be performed to obtain TIL for subsequent lymphocyte cultures. TIL will be grown and expanded for this trial generally as described in Example 3, and the age (in days) of the cells administered to each of 25 patients is as follows: 20, 24, 26, 26, 26, 26, 27, 27, 28, 28, 29, 29, 29, 29, 32, 34, 34, 34, 34, 34, 35, 35, 35, 36, and 36. The average age of the cells is 30 days. As in the prior cell infusion protocols, volunteers on the Surgery Branch protocol 03-C-0277, "Cell Harvest and Preparation for Surgery Branch Adoptive Cell Therapy Protocols" will donate whole blood and serum to be isolated and used in cell culture according to the strict safety criteria outlined in 03-C-0277. Volunteers will also undergo apheresis to obtain mononuclear cells to be used as feeder cells in cell culture. The procedures used are those in routine use in the Department of Transfusion Medicine in the Clinical Center. Separate consents will be obtained from all blood and apheresis volunteers.

Prior to patient enrollment on this study, TIL cultures will be monitored regularly, and at the earliest feasible time, TIL will be assessed for potency by OKT3-stimulated IFN release (greater than 200 pg/ml per $10^5$ cells). Once cells have been deemed eligible for use in this trial, patients will be consented on this study and enrolled. The patient must meet the eligibility criteria prior to administration of the preparative regimen. Growth and expansion of the final product will be performed after the patient has consented to participate in this specific study.

3.1.2 Treatment Phase

Once cells exceed the potency requirement and are projected to exceed $5\times10^8$ cells (measured by visual microscopic count), (approximately 7 days after the REP procedure has been initiated) the patient will receive the lymphocyte depleting preparative regimen consisting of fludarabine and cyclophosphamide (in cohorts 1 and 2), followed by infusion of up to $3\times10^{11}$ lymphocytes (minimum of $1\times10^9$) and the administration of aldesleukin. In cohort 3, patients will receive a lymphocyte depleting preparative regimen consisting of cyclophosphamide and fludarabine plus 600 cGy total body irradiation followed in one to four days by intravenous infusion of up to $3\times10^{11}$ lymphocytes (minimum of $1\times10^9$) and the administration of aldesleukin.

Approximately 4-6 weeks after cell infusion, patients will undergo a complete tumor evaluation and evaluation of toxicity and immunologic parameters. This will comprise one course of therapy. Patients will receive no other experimental agents while on this protocol.

Drug Administration:

3.2.1 For Cohorts 1 (closed) and 2: Preparative Regimen with Cyclophosphamide and Fludarabine On Day −7 and −6, patients will be treated as set forth in Table 13.

TABLE 13

| Time | Treatment |
| --- | --- |
| 1 am | Hydrate: Begin hydration with 0.9% Sodium Chloride Injection containing 10 meq/L of potassium chloride at 2.6 ml/kg/hr (starting 11 hours pre-cyclophosphamide and continue hydration until 24 hours after last cyclophosphamide infusion) |
| 11 am | Ondansetron (0.15 mg/kg/dose [rounded to the nearest even mg dose between 8 mg and 16 mg based on patient weight] IV every 8 hours × 3 days) will be given for nausea. Furosemide 10-20 mg iv. |
| 12 pm (noon) | Cyclophosphamide 60 mg/kg/day × 2 days IV in 250 ml D5W with mesna 15 mg/kg/day × 2 days over 1 hr. If patient is obese (BMI > 35) drug dosage will be calculated using practical weight. |
| 1 pm | Begin to monitor potassium level every 12 hours until hydration is stopped. KCl will be adjusted to maintain serum potassium levels in the normal range. |
| 1 pm | Begin mesna infusion at 3 mg/kg/hour intravenously diluted in a suitable diluent over 23 hours after each cyclophosphamide dose. If patient is obese (BMI > 35) drug dosage will be calculated using practical weight. |

On Day −5, IV hydration is stopped (24 hours after last cyclophosphamide dose). If urine output is less than 1.5 ml/kg/hr, an additional 20 mg furosemide iv is given. If body weight is greater than 2 kg over pre cyclophosphamide value, additional furosemide 20 mg iv is given.

On Day −5 to Day −1, Fludarabine 25 mg/m$^2$/day IVPB is given daily over 30 minutes for 5 days. If patient is obese (BMI>35) drug dosage will be calculated using practical weight.

3.2.2 Cell Administration (for Cohorts 1 (closed) and 2):

Day 0 (One to Four Days after the Last Dose of Fludarabine):

Cells will be infused intravenously (i.v.) on the Patient Care Unit over 20 to 30 minutes (between one and four days after the last dose of fludarabine). Cell infusions will be given as an inpatient.

Aldesleukin 720,000 IU/kg IV (based on total body weight) over 15 minute every eight hours beginning within 24 hours of cell infusion and continuing for up to 5 days (maximum of 15 doses.)

Day 1-4 (Day 0 is the Day of Cell Infusion):

Beginning on day 1 or 2, filgrastim will be administered subcutaneously at a dose of 5 mcg/kg/day (not to exceed 300 mcg/day). Filgrastim administration will continue daily until neutrophil count >1.0×10$^9$/L×3 days or >5.0×10$^9$/L.

Aldesleukin 720,000 IU/kg IV (based on total body weight) over 15 minutes is given every eight hours for up to 5 days.

3.2.3 For Cohort 3 only: Preparative Regimen with Cyclophosphamide, Fludarabine and TBI On Day −6 and −5, patients will be treated as set forth in Table 13.

On Day −6 to Day −2, Fludarabine 25 mg/m$^2$/day IVPB is administered daily over 15-30 minutes for 5 days. If the patient is obese (BMI>35) drug dosage will be calculated using practical weight. (The fludarabine will be started approximately 1-2 hours after the cyclophosphamide and mesna on Days −6 and −5). To allow as much time between the last dose of fludarabine and the administration of the cell treatment, the timing of the fludarabine administration can be moved to an hour earlier each day.)

On Day −4, IV hydration is stopped (24 hours after last cyclophosphamide dose). If urine output <1.5 ml/kg/hr, additional 20 mg furosemide iv is given. If body weight >2 kg over pre cyclophosphamide value give additional furosemide 20 mg iv.

On Day −2 and Day −1, prior to TBI, patients will receive a single dose of IV ondansetron (ondansetron 0.15 mg/kg IV [rounded to the nearest even mg dose between 8 mg and 16 mg based on patient weight]×1 dose pre-TBI). Patients will receive 2Gy of TBI (see Sec 3.2.5) twice on day −2 and once on day −1 (total dose 6 Gy) at a rate of 0.07 Gy/minute using a linear accelerator in Radiation Oncology.

3.2.4 Cell Administration Cohort 3 Only)

Day 0 (One to Three Days after the Last Dose of TBI):

CD4$^+$ depleted young TIL cells will be infused intravenously (i.v.) on the Patient Care Unit over 20 to 30 minutes. Cell infusions will be given as an inpatient. Aldesleukin 720,000 IU/kg IV (based on total body weight) over 15 minute every eight hours beginning within 24 hours of cell infusion and continuing for up to 5 days (maximum of 15 doses.). Beginning on day 0 or 1, filgrastim will be administered subcutaneously at a dose of 5 mcg/kg/day (not to exceed 300 mcg/day). Filgrastim administration will continue daily until neutrophil count >1.0×10$^9$/L×3 days or >5.0×10$^9$/L.

Day 1: (Day 0 is the day of TIL Infusion)

The cryopreserved autologous CD34$^+$ selected stem cell product will be thawed and administered intravenously immediately. The minimum dose will be >2×10$^6$ CD34$^+$ cells per kg. CD34$^+$ cells are returned on day 1 to maximize the exchange only of the transferred T cells (day 0) to the homeostatic environment resulting from lymphodepletion.

Day 1-4:

Aldesleukin 720,000 IU/kg IV (based on total body weight) over 15 minutes every eight hours for up to 5 days.

3.2.5 Total Body Irradiation (TBI) (for Cohort 3 Only)

All patients should be treated with a linear accelerator using energies higher than 4MV. It is anticipated that TBI will be delivered on day −2, −1. TBI will be delivered with lateral fields using extended SSD/SAD values of 200-500 cm (depending on machine/vault size). Tissue compensation for the lung and head and neck regions may be employed to maximize dose homogeneity. Patients will be treated with TBI to a total dose of 600 cGy delivered in 200 cGy fractions twice on day −2, at least 6 hours apart and once on day −1.

Occasionally, the total dose/technique of TBI may require modifications due to patient factors (unexpected or severe (grade 4-5) adverse events, serious medical illnesses not conducive to stable patient transfer, patient refusal, etc.) or treatment factors (linear accelerator machine offline, etc.). Modifications to the radiation treatment will be at the discretion of the treating radiation oncologist and will be discussed with the Principal Investigator or Study Chairperson.

3.2.6 Infection Prophylaxis (all Cohorts)

3.2.6.1 *Pneumocystis Carinii Pneumonia*

All patients will receive the fixed combination of trimethoprim and sulfamethoxazole [SMX] as double strength (DS) tab (DS tabs=TMP 160 mg/tab, and SMX 800 mg/tab) P.O. daily three times a week on non-consecutive days, beginning on day −6 and stopping when the CD4 count is above 200 and for at least 6 months post chemotherapy.

Pentamidine will be substituted for TMP/SMX-DS in patients with sulfa allergies. It will be administered aerosolized at 300 mg per nebulizer within one week prior to admission and continued monthly until CD4 count is above 200 and for at least 6 months post chemotherapy.

3.2.6.2 Herpes Virus Prophylaxis

Patients with positive HSV serology will be given valacyclovir orally at a dose of 500 mg daily the day after chemotherapy ends, or acyclovir, 250 mg/m$^2$ IV q 12 hrs if the patient is not able to take medication by mouth which is continued until absolute neutrophil count is greater than 1000/mm$^3$. Reversible renal insufficiency has been reported with IV but not oral acyclovir. Neurologic toxicity including delirium, tremors, coma, acute psychiatric disturbances, and abnormal EEGs have been reported with higher doses of acyclovir. Should this occur, a dosage adjustment will be made or the drug will be discontinued. Acyclovir will not be used concomitantly with other nucleoside analogs which interfere with DNA synthesis, e.g., ganciclovir. In renal disease, the dose is adjusted as per product labeling.

3.2.6.3 Fungal Prophylaxis (Fluconazole)

Patients will start Fluconazole 400 mg p.o. the day after chemotherapy concludes and continue until the absolute neutrophil count is greater than 1000/mm$^3$. The drug may be given IV at a dose of 400 mg in 0.9% sodium chloride USP daily in patients unable to take it orally.

3.2.6.4 Empiric Antibiotics

Patients will start on broad-spectrum antibiotics, either a 3$^{rd}$ or 4$^{th}$ generation cephalosporin or a quinolone for fever of 38.3° C. once or two temperatures of 38.0° C. or above at least one hour apart, and an ANC <500/mm$^3$. Aminoglycosides should be avoided unless clear evidence of sepsis. Infectious disease consultation will be obtained for all patients with unexplained fever or any infectious complications.

3.2.7 Blood Product Support (for all Cohorts)

Using daily CBCs as a guide, the patient will receive platelets and packed red blood cells (PRBC's) as needed. Attempts will be made to keep Hb >8.0 gm/dl, and pits >20,000/mm$^3$. Note, patients with brain metastasis will be transfused when platelets fall below 50,000/mm$^3$. All blood products with the exception of the stem cell product will be irradiated. Leukocyte filters will be utilized for all blood and platelet transfusions to decrease sensitization to transfused WBCs and decrease the risk of CMV infection.

3.2.8 Aldesleukin: Intravenous Administration (for all Cohorts)

Aldesleukin will be administered at a dose of 720,000 IU/kg (based on total body weight) as an intravenous bolus over a 15 minute period every eight hours beginning on the day of cell infusion and continuing for up to 5 days (maximum 15 doses). Doses may be skipped depending on patient tolerance. Doses will be skipped if patients reach Grade III or IV toxicity due to aldesleukin except for the reversible Grade III toxicities common to aldesleukin such as, for example, diarrhea, nausea, vomiting, hypotension, skin changes, anorexia, mucositis, dysphagia. Toxicities will be managed. If these toxicities can be easily reversed within 24 hours by supportive measures then additional doses may be given. Additional instances may arise when in the clinical judgment of the attending physician, based on the extensive clinical experience in the Surgery Branch with aldesleukin, when doses of aldesleukin may be skipped. If greater than 2 doses of aldesleukin are skipped, aldesleukin administration will be stopped. Aldesleukin will be administered as an inpatient and will be purchased by the NIH Clinical Pharmacy Department from commercial sources.

3.3 On-Study Evaluation

Within 14 days prior to starting the preparative regimen, patients will have a complete blood count, electrolytes, BUN, creatinine, liver function tests and serum chemistries performed. If any results are beyond the criteria established for eligibility, the patient will not proceed until the abnormalities can be resolved.

For patients in cohort 3 only, 15 mL of clean catch urine will be collected to be tested.

During the Preparative Regimen: DAILY

Patients will be evaluated on the basis of: Complete Blood Count; Chem 20: [Sodium (Na), Potassium (K), Chloride (Cl), Total CO$_2$ (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, LD, Total Protein, Total CK, Uric Acid]; and Urinalysis. CMV antigen assay will be assessed if clinically indicated (e.g., unexplained fevers, pulmonary changes). For patients in cohort 3 only, 15 mL of clean catch urine to be tested will be collected at one week after TBI, approximately 1 month after TBI and 6 months after TBI.

After Cell Infusion

After cell infusion vital signs will be monitored hourly until stable and then routinely (every 4 hours) unless otherwise clinically indicated.

During and after Aldesleukin Administration (Until Hospital Discharge)—Every 1-2 Days Patients will be evaluated by Complete Blood Count and Chem 20: [Sodium (Na), Potassium (K), Chloride (Cl), Total CO2 (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, LD, Total Protein, Total CK, Uric Acid].

3.3.5 Additional Research Evaluations

Once total lymphocyte count is greater than 200/mm$^3$, the following samples will be drawn and sent to the TIL lab on Monday, Wednesday and Friday: 5 CPT tubes (10 ml each) and 1 SST tube (10 ml).

Biopsies of tumor tissue or lymph node may be performed but are not required during the course of therapy. Studies will be performed to evaluate the antigen expression by the tumor and to evaluate the reactivity of lymphocytes grown from these biopsies. Biopsies will be performed at baseline, after the course of therapy, and in the event of response. These biopsies will only be performed if minimal morbidity is expected based on the procedure performed and the granulocyte and platelet count.

Peripheral blood lymphocytes (PBL) will be purified by centrifugation on a Ficoll cushion, then evaluated for function and phenotype. Lymphocytes may be tested by cytolysis assays, cytokine release, limiting dilution analysis and by other experimental studies. Immunological monitoring will consist of quantifying T cells reactive with HLA-matched tumor cells using established techniques such as intracellular FACS, cytokine release assays, and Elispot assays. Immunological assays will be standardized by the inclusion of 1) pre-infusion PBMC and 2) an aliquot of the T cells cryopreserved at the time of infusion. TCR gene usage may be quantitated in samples using conventional sequencing techniques of the T cell receptor variable regimen of the beta chain.

A variety of tests including evaluation of specific lysis and cytokine release, intracellular FACS of cytokine production, ELISA-spot assays, and lymphocyte subset analysis may be used to compare evaluate the immunological correlates of treatment. In general, differences of 2 to 3 fold in these assays are indicative of true biologic differences. In addition, measurement of CD4+ and CD8+ T cells will be conducted and studies of cell persistence in the circulation will be conducted by using PCR assays capable of detecting the unique sequence of the T-cell receptor rearrangements of the infused cells.

Samples of all infused cell products will be cryopreserved, and extensive retrospective analysis of infused cell phenotype and function will be performed to attempt to find in vitro characteristics of the infused cells which correlate with in vivo antitumor activity. Analyses of TIL samples will include evaluation of the activity, specificity, and telomere length of the infused TIL.

Blood and tissue specimens collected in the course of this research project may be banked and used in the future to investigate new scientific questions related to this study. However, this research may only be done if the risks of the new questions were covered in the consent document. If new risks are associated with the research (e.g., analysis of germ line genetic mutations) the principal investigator must amend the protocol and obtain informed consent from all research subjects.

10 cc serum and separated lymphocytes from blood will be obtained prior to cell infusion and following each infusion if possible and cryopreserved for subsequent testing; leukapheresis will be utilized to obtain peripheral blood lymphocytes in patients, pretreatment and may be repeated at approximately 4-6 weeks after the cell infusions and will consist of a 7.5-liter exchange to last approximately three hours. All patients undergoing pheresis will sign informed consent.

3.4 Post Treatment Evaluation (Follow-Up) 4-6 Weeks Following Cell Infusion

Patients will be evaluated on the basis of a physical examination, toxicity assessment, and CT of the chest, abdomen and pelvis. This end of course evaluation will be used to determine tumor response. If clinically indicated, other scans or x-rays may be performed, e.g., brain MRI, bone scan.

A 5 liter apheresis will be performed or 60 ml of blood will be obtained. Peripheral blood mononuclear cells will be cryopreserved so that immunologic testing may be performed.

For patients in cohort 3 only, 15 mL of clean catch urine to be tested will be collected approximately 1 month after TBI and 6 months after TBI.

If the patient has SD or tumor shrinkage, repeat complete evaluations will be performed every 1-3 months, or as clinically indicated including obtaining 60 ml of blood for immunologic testing.

4.0 Supportive Care

Concomitant medications to control side-effects of therapy will be given. Meperidine (25-50 mg) will be given intravenously if severe chilling develops. Other supportive therapy will be given as required and may include acetaminophen (650 mg q4h), indomethacin (50-75 mg q6h) and ranitidine (150 mg q 12h). Patients who require transfusions will receive irradiated blood products. Additional antiemetic therapy will be administered for breakthrough nausea and vomiting.

5.0 Data Collection and Evaluation
5.1 Response Criteria
5.1.2. Evaluation of Target Lesions All measurable lesions up to a maximum of 10 lesions representative of all involved organs should be identified as target lesions and recorded and measured at baseline. Target lesions should be selected on the basis of their size (lesions with the longest diameter) and their suitability for accurate repetitive measurements (either by imaging techniques or clinically). A sum of the longest diameter (LD) for all target lesions will be calculated and reported as the baseline sum LD. The baseline sum LD will be used as reference to further characterize the objective tumor response of the measurable dimension of the disease.

Responses are determined as set forth in Table 14. A Complete Response (CR) is considered to be the disappearance of all target lesions. A Partial Response (PR) is considered to be at least a 30% decrease in the sum of the longest diameter (LD) of target lesions taking as reference the baseline sum LD. Progression (PD) is considered to be at least a 20% increase in the sum of LD of target lesions taking as reference the smallest sum LD recorded since the treatment started or the appearance of one or more new lesions. Stable Disease (SD) is considered to be either sufficient shrinkage to qualify for PR nor sufficient increase to qualify for PD taking as references the smallest sum LD.

5.1.2. Evaluation of Non-Target Lesions

All other lesions (or sites of disease) should be identified as non-target lesions and should also be recorded at baseline. Measurements are not required, and these lesions should be followed as "present" or "absent."

Responses are determined as set forth in Table 14. Complete Response (CR) is considered to be the disappearance of all non-target lesions and normalization of tumor marker level. Non-Complete Response is considered to be the persistence of one or more non-target lesions. Progression (PD) is considered to be the appearance of one or more new lesions and/or unequivocal progression of existing non-target lesions.

5.1.3 Evaluation of Best Overall Response

The best overall response is the best response recorded from the start of the treatment until disease progression/recurrence (taking as reference for progressive disease the smallest measurements recorded since the treatment started). The patient's best response assignment will depend on the achievement of both measurement and confirmation criteria.

TABLE 14

| Target Lesions | Non-Target Lesions | New Lesions | Overall Response |
| --- | --- | --- | --- |
| CR | CR | No | CR |
| CR | Non-CR/Non-PD | No | PR |
| PR | Non-PD | No | PR |
| SD | Non-PD | No | SD |
| PD | Any | Yes or No | PD |
| Any | PD | Yes or No | PD |
| Any | Any | Yes | PD |

5.1.4 Confirmatory Measurement/Duration of Response Confirmation

To be assigned a status of PR or CR, changes in tumor measurements must be confirmed by repeat studies that should be performed at least 4 weeks after the criteria for response are first met. In the case of SD, follow-up measurements must have met the SD criteria at least once after study entry at a minimum interval of 6-8 weeks.

Duration of Overall Response

The duration of overall response is measured from the time measurement criteria are met for CR/PR (whichever is first recorded) until the first date that recurrent or progressive disease is objectively documented (taking as reference for progressive disease the smallest measurements recorded since the treatment started).

The duration of overall complete response is measured from the time measurement criteria are first met for CR until the first date that recurrent disease is objectively documented.

Duration of Stable Disease

Stable disease is measured from the start of the treatment until the criteria for progression are met, taking as reference the smallest measurements recorded since the treatment started.

Pharmaceutical Information

Interleukin-2 (Aldesleukin, Proleukin, Recombinant Human Interleukin 2)

How Supplied:

Interleukin-2 (aldesleukin) is manufactured by the Chiron Corporation, Emeryville, Calif., and will be purchased by the NIH Clinical Pharmacy Department from commercial sources.

Formulation/Reconstitution:

Aldesleukin, NSC #373364, is provided as single-use vials containing 22 million IU (−1.3 mg) IL-2 as a sterile, white to off-white lyophilized cake plus 50 mg mannitol and 0.18 mg sodium dodecyl sulfate, buttered with approximately 0.17 mg monobasic and 0.89 mg dibasic sodium phosphate to a pH of 7.5 (range 7.2 to 7.8). The vial is reconstituted with 1.2 mL of Sterile Water for Injection, USP, and the resultant concentration is 18 million IU/ml or 1.1 mg/mL. Diluent should be directed against the side of the vial to avoid excess foaming. Swirl contents gently until completely dissolved. Do not shake. Since vials contain no preservative, reconstituted solution should be used with 24 hours.

Storage:

Intact vials are stored in the refrigerator (2°-8° C.) protected from light. Each vial bears an expiration date.

Dilution/Stability:

Reconstituted aldesleukin should be further diluted with 50 mL of 5% Human Serum Albumin (HSA). The HSA should be added to the diluent prior to the addition of RIL-2. Dilutions of the reconstituted solution over a 1000-fold range (i.e., 1 mg/mL to 1 mcg/mL) are acceptable in either glass bottles or polyvinyl chloride bags. Aldesleukin is chemically stable for 48 hours at refrigerated and room temperatures, 2°-30° C.

Administration:

The dosage will be calculated based on total body weight. The final dilution of aldesleukin will be infused over 15 minutes. Aldesleukin will be administered as an inpatient.

Toxicities:

Expected toxicities of aldesleukin are listed in the product label. Grade III toxicities common to aldesleukin include diarrhea, nausea, vomiting, hypotension, skin changes, anorexia, mucositis, dysphagia, or constitutional symptoms and laboratory changes.

8.2 Fludarabine

Description:

Fludarabine phosphate is a synthetic purine nucleoside that differs from physiologic nucleosides in that the sugar moiety is arabinose instead of ribose or deoxyribose. Fludarabine is a purine antagonist antimetabolite.

How Supplied:

It will be purchased by the NIH Clinical Pharmacy Department from commercial sources. Fludarabine is supplied in a 50 mg vial as a fludarabine phosphate powder in the form of a white, lyophilized solid cake.

Stability:

Following reconstitution with 2 mL of sterile water for injection to a concentration of 25 mg/ml, the solution has a pH of 7.7. The fludarabine powder is stable for at least 18 months at 2-8° C.; when reconstituted, fludarabine is stable for at least 16 days at room temperature. Because no preservative is present, reconstituted fludarabine will typically be administered within 8 hours. Specialized references should be consulted for specific compatibility information. Fludarabine is dephosphorylated in serum, transported intracellularly and converted to the nucleotide fludarabine triphosphate; this 2-fluoro-ara-ATP molecule is thought to be required for the drug's cytotoxic effects. Fludarabine inhibits DNA polymerase, ribonucleotide reductase, DNA primase, and may interfere with chain elongation, and RNA and protein synthesis.

Storage:

Intact vials should be stored refrigerated (2-8° C.).

Administration:

Fludarabine is administered as an IV infusion in 100 ml 0.9% sodium chloride, USP over 15 to 30 minutes. The doses will be based on body surface area (BSA). If patient is obese (BMI>35) drug dosage will be calculated using practical weight.

Toxicities:

At doses of 25 mg/m$^2$/day for 5 days, the primary side effect is myelosuppression; however, thrombocytopenia is responsible for most cases of severe and life-threatening hematologic toxicity. Serious opportunistic infections have occurred in CLL patients treated with fludarabine. Hemolytic anemia has been reported after one or more courses of fludarabine with or without a prior history of a positive Coomb's test; fatal hemolytic anemia has been reported. In addition, bone marrow fibrosis has been observed after fludarabine therapy. Other common adverse effects include malaise, fever, chills, fatigue, anorexia, nausea and vomiting, and weakness. Irreversible and potentially fatal central nervous system toxicity in the form of progressive encephalopathy, blindness, and coma is only rarely observed at the currently administered doses of fludarabine. More common neurologic side effects at the current doses of fludarabine include weakness, pain, malaise, fatigue, paresthesia, visual or hearing disturbances, and sleep disorders. Adverse respiratory effects of fludarabine include cough, dyspnea, allergic or idiopathic interstitial pneumonitis. Tumor lysis syndrome has been rarely observed in fludarabine treatment of CLL. Treatment on previous adoptive cell therapy protocols in the Surgery Branch have caused persistently low (below 200) CD4 counts, and one patient developed polyneuropathy manifested by vision blindness, and motor and sensory defects.

Cyclophosphamide

Description:

Cyclophosphamide is a nitrogen mustard-derivative alkylating agent. Following conversion to active metabolites in the liver, cyclophosphamide functions as an alkyating agent; the drug also possesses potent immunosuppressive activity. The serum half-life after IV administration ranges from 3-12 hours; the drug and/or its metabolites can be detected in the serum for up to 72 hours after administration.

How Supplied:

Cyclophosphamide will be obtained from commercially available sources by the Clinical Center Pharmacy Department.

Stability:

Following reconstitution as directed with sterile water for injection, cyclophosphamide is stable for 24 hours at room temperature or 6 days when kept at 2-8° C.

Administration:

It will be diluted in 250 ml D5W and infused over one hour. The dose will be based on the patient's body weight. If patient is obese (BMI>35) drug dosage will be calculated using practical weight.

Toxicities:

Hematologic toxicity occurring with cyclophosphamide usually includes leukopenia and thrombocytopenia. Anorexia, nausea and vomiting, rash and alopecia occur, especially after high-dose cyclophosphamide; diarrhea, hemorrhagic colitis, infertility, and mucosal and oral ulceration have been reported. Sterile hemorrhagic cystitis occurs in about 20% of patients; severity can range from microscopic hematuria to extensive cystitis with bladder fibrosis. Although the incidence of hemorrhagic cystitis associated with cyclophosphamide appears to be lower than that associated with ifosfamide, mesna (sodium 2-mercaptoethanesulfonate) has been used prophylactically as a uroprotective agent in patients receiving cyclophosphamide. Prophylactic mesna is not effective in preventing hemorrhagic cystitis in all patients. Patients who receive high dose cyclophosphamide may develop interstitial pulmonary fibrosis, which can be fatal. Hyperuricemia due to rapid cellular destruction may occur, particularly in patients with hematologic malignancy. Hyperuricemia may be minimized by adequate hydration, alkalinization of the urine, and/or administration of allopurinol. If allopurinol is administered, patients should be watched closely for cyclophosphamide toxicity (due to allopurinol induction of hepatic microsomal enzymes). At high doses, cyclophosphamide can result in a syndrome of inappropriate antidiuretic hormone secretion; hyponatremia with progressive weight gain without edema occurs. At high doses, cyclophosphamide can result in cardiotoxicity. Deaths have occurred from diffuse hemorrhagic myocardial necrosis and from a syndrome of acute myopericarditis; in such cases, congestive heart failure may occur within a few days of the first dose. Other consequences of cyclophosphamide cardiotoxicity include arrhythmias, potentially irreversible cardiomyopathy, and pericarditis. Other reported adverse effects of cyclophosphamide include headache, dizziness, and myxedema; faintness, facial flushing, and diaphoresis have occurred following IV administration. Mesna (sodium 2-mercaptoethanesulphonate; given by IV injection) is a synthetic sulfhydryl compound that can chemically interact with urotoxic metabolites of cyclophosphamide (acrolein and 4-hydroxycyclophosphamide) to decrease the incidence and severity of hemorrhagic cystitis.

Mesna (Sodium 2-mercaptoethanesulfonate, Mesnum, Mesnex, NSC-113891)

Description:

Mesna will be obtained commercially by the Clinical Center Pharmacy Department and is supplied as a 100 mg/ml solution.

Storage:

Intact ampoules are stored at room temperature.

Stability:

Diluted solutions (1 to 20 mg/mL) are physically and chemically stable for at least 24 hours under refrigeration. Mesna is chemically stable at room temperature for 48-72 hours in D5W, 48-72 hour in D5W/0.45% NaCl, or 24 hours in 0.9% NaCl.

Administration:

Dilute to concentrations less than or equal to 20 mg mesna/ml fluid in D5W or 0.9% NaCl and to be administered intravenously as a continuous infusion. If patient is obese (BMI>35) drug dosage will be calculated using practical weight. Toxicities include nausea, vomiting and diarrhea.

Filgrastim (Granulocyte Colony-Stimulating Factor, G-CSF, Filgrastim, Neupogen)

Filgrastim will be obtained commercially by the Clinical Center Pharmacy Department and is supplied in 300 ug/ml and 480 ug/1.6 ml vials. G-CSF should be refrigerated and not allowed to freeze. The product bears the expiration date. The product should not be shaken. It is generally stable for at least 10 months when refrigerated. The appropriate dose is drawn up into a syringe. G-CSF will be given as a daily subcutaneous injection. The side effects of G-CSF are skin rash, myalgia and bone pain, an increase of preexisting inflammatory conditions, enlarged spleen with occasional associated low platelet counts, alopecia (with prolonged use) elevated blood chemistry levels.

Trimethoprim and Sulfamethoxazole Double Strength (TMP/SMX DS)

TMP/SMX DS will be obtained by the Clinical Center Pharmacy Department from commercial sources. It will be used for the prevention of PCP pneumonia. The oral dose is 1 tablet PO daily three times a week (on NON-consecutive days) beginning on day −7 and continuing for at least 6 months and until the CD4 count is greater than 200 on 2 consecutive lab studies. Like other sulfa drugs, TMP/SMX DS can cause allergies, fever, photosensitivity, nausea, and vomiting. Allergies typically develop as a widespread itchy red rash with fever eight to fourteen days after beginning the standard dose. Neutropenia, a reduction in the number of neutrophils, can also occur.

Aerosolized Pentamidine in Place of TMP/SMX DS:

Patients with sulfa allergies will receive aerosolized Pentamidine 300 mg per nebulizer within one week prior to admission and continued monthly until the CD4 count is above 200 on two consecutive follow up lab studies and for at least 6 months post chemotherapy. Pentamidine Isethionate will be obtained by the Clinical Center Pharmacy Department from commercial sources. It will be used to prevent the occurrence of PCP infections. It is supplied in 300 mg vials of lyophilized powder and will be administered via nebulizer. Toxicities reported with the use of Pentamidine include metallic taste, coughing, bronchospasm in heavy smokers and asthmatics; increased incidence of spontaneous pneumothorax in patients with previous PCP infection or pneumatoceles, or hypoglycemia.

Herpes Virus Prophylaxis

Valacyclovir (Valtrex)

Valacyclovir will be obtained by the Clinical Center Pharmacy Department from commercial sources. It will be used orally to prevent the occurrence of herpes virus infections in patients with positive HSV serology. It is supplied in 500 mg tablets. Valacyclovir will be started the day after the last dose of fludarabine at a dose of 500 mg orally daily if the patient is able to tolerate oral intake. See package insert for dosing adjustments in patients with renal impairment. Common side effects include headache, upset stomach, nausea, vomiting, diarrhea or constipation. Rare serious side effects include hemolytic uremic syndrome and thrombotic thrombocytopenic purpura.

Acyclovir

Acyclovir will be obtained by the Clinical Center Pharmacy Department from commercial sources. It will be used to prevent the occurrence of herpes virus infections in patients who cannot take oral medications. It is supplied as powder for injection in 500 mg/vials. Reconstitute in 10 mL of sterile water for injection to a concentration of 50 mg/mL. Reconstituted solutions should be used within 12 hours. IV solutions should be diluted to a concentration of 7 mg/mL or less and infused over 1 hour to avoid renal damage. Reversible renal insufficiency has been reported with IV but not oral acyclovir. Neurologic toxicity including delirium, tremors, coma, acute psychiatric disturbances, and abnormal EEGs have been reported with higher doses of acyclovir. Should this occur, a dosage adjustment will be made or the drug will be discontinued. Stomach upset, headache or nausea, rash or hives; peripheral edema; pain, elevated liver function tests; and leukopenia, diarrhea, lymphadenopathy, myalgias, visual abnormalities and elevated creatinine have been reported. Hair loss from prolonged use has been reported. Acyclovir will not be used concomitantly with other nucleoside analogs which interfere with DNA synthesis, e.g. ganciclovir. In renal disease, the dose is adjusted as per product labeling.

Fluconazole

Fluconazole will be obtained by the Clinical Center Pharmacy Department from commercial sources. It will be used to prophylax against fungal infections. It is available in 200 mg tablets. It can cause headache, nausea, vomiting, diarrhea or abdominal pain, and liver damage which may be irreversible. It can cause rashes and itching, which in rare cases has caused Stevens Johnson Syndrome. It has several significant drug interactions. The package insert should be consulted prior to prescribing. For IV administration in patients who cannot tolerate the oral preparation, Fluconazole comes in 2 MG/ML solution for injection, and prepared according to Clinical Center Pharmacy standard procedures. It should be administered at a maximum IV rate of 200 mg/hr.

OKT3

OKT3 will be obtained by the Surgery Branch Laboratory from commercial sources.

Formulation:

Muromonab-CD3 (Ortho), NSC #618843, is provided as a sterile, clear, colorless solution at a concentration of 1 mg/ml in 5 ml ampoules. The solution may contain a few fine, translucent protein particles. The antibody is dissolved in a buffered solution at pH of 6.5 to 7.5. The solution contains 2.25 mg of monobasic sodium phosphate, 9 mg of dibasic sodium phosphate, 43 mg of sodium chloride and 1 mg of polysorbate 80 per 5 ml of water for injection.

Storage/Stability:

Ampules should be stored in a refrigerator at 2-8° C. Solution should not be frozen or shaken. Each ampule bears an expiration date.

Support Medications

Ondansetron Hydrochloride

Ondansetron hydrochloride will be obtained by the Clinical Center Pharmacy Department from commercial sources. It will be used to control nausea and vomiting during the chemotherapy preparative regimen. It can cause headache, dizziness, myalgias, drowsiness, malaise, and weakness. Less common side effects include chest pain, hypotension, pruritis, constipation and urinary retention. Consult the package insert for specific dosing instructions.

Furosemide

Furosemide will be obtained by the Clinical Center Pharmacy Department from commercial sources. It will be used to enhance urine output during the chemotherapy preparative regimen with cyclophosphamide. Adverse effects include dizziness, vertigo, paresthesias, weakness, orthostatic hypotension, photosensitivity, rash and pruritis. Consult the package insert for a complete list of all side effects.

Preliminary Results

Twenty-five patients underwent treatment including administration of young TIL that were rapidly expanded and administered (ages of young TIL in days: 20, 24, 26, 26, 26, 26, 27, 27, 28, 28, 29, 29, 29, 29, 32, 34, 34, 34, 34, 34, 35, 35, 35, 36, 36) following lymphodepletion with cyclophosphamide and fludarabine. Patients then received high dose interleukin (IL)-2 therapy. Six patients (24%) experienced an objective response to young TIL therapy. There were significant toxicities associated with TIL administration including seven instances of adverse events requiring intubation and one treatment related mortality. Subsequently permission was sought and obtained to amend the protocol to enrich the TIL population for $CD8^+$ cells prior to rapid expansion, as set forth in Example 12.

This example demonstrated a method of promoting regression of a cancer in a mammal comprising (i) culturing autologous T cells; (ii) rapidly expanding the cultured T cells; (iii) administering to the mammal nonmyeloablative lymphodepleting chemotherapy; and (iv) after administering nonmyeloablative lymphodepleting chemotherapy, administering to the mammal the expanded T cells, wherein the T cells administered to the mammal are about 19 to about 35 days old, whereupon the regression of the cancer in the mammal is promoted.

Example 12

This example demonstrates the generation of CD8+ enriched young TIL. Patients with metastatic melanoma underwent biopsy and as much of the sample as possible was processed to a single cell suspension for generation of young TIL as described in Example 1, Dudley et al. *J. Immunother.* 26(4):332-42 (2003) and as further detailed in this example.

Acquisition of Samples for Initiation of TIL.

The specimen is received in the laboratory as soon as possible after surgery. All appropriate procurement documentation must accompany clinical specimens. Once the specimen arrives in the laboratory, all downstream processing is performed in a laminar flow biological safety cabinet. The sample is assigned a unique tumor accession number. With a clinical pathologist present, tissue is dissected that will remain in the Cell Production Laboratory free from normal, necrotic, and excess sample, and the latter is returned to the pathology laboratory for diagnosis. Additional research samples are taken for cytopathology, immunocytochemistry, and RNA analysis as necessary. The remaining tumor sample is now ready to prepare as a single cell suspensions.

Preparation of Single Cell Suspension.

Samples smaller than 5 g may be prepared by physical disaggregation in enzymes media using a gentleMACS™ Dissociator (Miltenyi Biotec, Auburn, Calif.) according to the manufacturers recommendations (Miltenyi). Samples larger than 5 g may be prepared by overnight enzymatic dissociation. Tissue should be diced into approximately 2 mm pieces and incubated in enzyme media with gentle stirring overnight. Enzyme media consists of RPMI 1640 (without serum) containing penicillin G (100 units/ml), streptomycin (100 µg/ml), gentamicin (50 µg/ml), Fungizone (1.25 µg/ml) (Bristol-Myers Squibb Co.; Princeton, N.J.), Collagenase (Type IV, Sigma, 1 mg/ml) and Pulmozyme® (Dornase, Genentech, San Francisco, Calif. ~30 units/ml). Disaggregated tumor samples should be passed through a 100 uM wire mesh or 70 uM disposable strainer, and washed three times prior to counting and plating. The single cell suspension was evaluated on a hemacytometer with lymphocytes and tumor cells determined based on size and morphology and viability determined by trypan blue staining. Cell composition is evaluated using morphological criteria to distinguish erythrocytes, lymphocytes and tumor cells. Tumor digest preparations that contain more than 50% dead cells or more than 80% erythrocytes may be further processed by Ficoll-hypaque step gradient enrichment.

Establishment of "bulk" TIL Cultures

TIL cultures are set up as described in Example 1. Briefly, cells are plated in 24-well sterile tissue culture plates, using $5.0 \times 10^5$ total viable nucleated cells/ml ($1.0 \times 10^6$ total viable cells/well, 2 ml/well) in complete medium (CM) containing 6000 IU/ml IL-2. The plates are incubated in a humidified incubator at 37° C., with 5% $CO_2$ in air. CM consists of RPMI-1640 with 10% human serum plus penicillin G (100 units/ml), streptomycin (100 µg/ml), gentamicin (50 µg/ml), and L-glutamine (146 µg/ml, 1 mM). The antibiotics may be omitted if a patient has relevant allergies. Other GMP quality media additives may be used when necessary (e.g. imipenem for potentially contaminated bowel lesions). Starting 5 days to one week after set up, half of the CM is replaced with fresh medium containing 6000 IU/ml IL-2. 2-3 media changes should be performed per week until the culture exceeds $1.0 \times 10^6$ lymphocytes/ml or becomes nearly confluent. As soon as TIL growth in the wells becomes confluent (and all adherent cells are eliminated), then individual culture wells should be pooled. Aliquots may be cryopreserved or the bulk TIL cells may be expanded further by re-plating at $0.7-1.5 \times 10^6$ lymphocytes/ml in CM containing IL-2 until sufficient cells are obtained for therapy. An aliquot of the bulk TIL should be examined by FACS to determine the percentages of $CD3^+$ and $CD8^+$ cells. The results are shown in Table 15.

CD8+ Enrichment and Clinical Scale Rapid Expansion Protocol (REP).

After minimum time in culture, successfully initiated "bulk" young TIL were CD8+ enriched (Miltenyi CliniMACS) (Prieto et al. J. Immunother. 33(5):547-556 (2010)) and rapidly expanded to clinical cell numbers (Dudley et al. J. Clin. Oncol. 23(10):2346-57 (2005); Riddell et al. J. Immunol. Methods 128(2):189-201 (1990)). The CD8+ enrichment has been described in detail (Prieto et al. J. Immunother. 33(5):547-556 (2010)) and is a modification of the Miltenyi CliniMACS procedure recommended by the manufacturer.

The rapid expansion protocol (REP) was modified from Riddell et al. J. Immunol. Methods 128(2):189-201 (1990) and has been described previously (Dudley et al. J. Clin. Oncol. 23(10):2346-57 (2005)). Briefly, $1 \times 10^6$ CD8+ enriched "responder" TIL are mixed with a 1:200 excess of 40Gy irradiated peripheral blood mononuclear "feeder" cells in 150 ml of "50/50" media containing 3000 IU/ml IL-2 and 30 ng/ml OKT3 (Ortho-McNeil®, Raritan, N.J.). 50/50 media consists of a 1:1 mixture of CM and AIM V (Invitrogen, Carlsbad Calif.). The mixture is added to a T175 flask and incubated in a vertical position in a humidified incubator at 37° C. in 5% $CO_2$ atmosphere. After 5 days, approximately ⅔ of the media is replaced with fresh 50/50 media containing IL-2 with no OKT3. After day 7, cells are maintained by splitting with AIM V media supplemented with 3000 IU/ml IL-2 as needed to maintain cell densities around $1 \times 10^6$ cells/ml. Cells are harvested by continuous flow centrifugation, washed, and infused on day 14.

Aliquots of infused samples were evaluated by FACS and cytokine release assays to determine lymphocyte phenotype and antigen specificity respectively using standard techniques (Dudley et al. J. Clin. Oncol. 23(10):2346-57 (2005)). The results are shown in Table 15. Table 15 sets forth the phenotype of bulk TIL cultures prior to CD8+ enrichment (TIL pre separation) and CD8+ enriched TIL products infused for therapy (Infusion Bag). "Cells" indicates the number of cells infused for treatment. Other numbers indicate the percent of total cells in the population expressing each marker ("NK" indicates CD56+ CD3− phenotype). Blank entries indicate data not obtained. NK cells (CD56+ CD3−) were not determined for patients who received NMA conditioning.

TABLE 15

| NMA Treatment ||||||| 6Gy TBI Treatment |||||||
| Cells | TIL Pre Separation ||| Infusion Bag || | Cells | TIL Pre Separation ||| Infusion Bag |||
| (x10e9) | CD4 | CD8 | NK | CD4 | CD8 | | (x10e9) | CD4 | CD8 | NK | CD4 | CD8 | NK |
|---|---|---|---|---|---|---|---|---|---|---|---|---|---|
| 84.6 | 6 | 69 | 10 | 0 | 98 | | 22.5 | 4 | 46 | 35 | 1 | 97 | 0 |
| 72.7 | 11 | 39 | 9 | 0 | 98 | | 32.8 | 26 | 54 | 16 | 1 | 100 | 0 |
| 56.9 | | | | | | | 11.8 | 12 | 57 | 11 | 0 | 99 | 0 |
| 24.5 | 32 | 44 | 19 | 5 | 97 | | 20.1 | | | | 1 | 99 | 0 |
| 23.8 | | | | 2 | 97 | | 41.2 | 49 | 25 | 22 | 2 | 97 | 0 |
| 34.2 | 19 | 85 | 11 | 1 | 98 | | 54.3 | 19 | 61 | 12 | 1 | 99 | 0 |
| 36.2 | 53 | 16 | 37 | 2 | 99 | | 48.3 | 48 | 11 | 30 | 3 | 98 | 0 |
| 47.6 | 5 | 81 | 37 | 0 | 99 | | 39.2 | 18 | 29 | 53 | 0 | 98 | 0 |
| 41.4 | 38 | 53 | 8 | 0 | 99 | | 35.9 | 14 | 30 | 44 | 1 | 98 | 0 |
| 55.9 | 22 | 80 | 3 | 0 | 100 | | 46.5 | 38 | 17 | 36 | 19 | 85 | 0 |
| 84.3 | 32 | 56 | 27 | 0 | 88 | | 51.7 | 5 | 82 | 9 | 0 | 99 | 0 |
| 55.1 | 25 | 67 | 18 | 1 | 95 | | 44.7 | 4 | 88 | 5 | 6 | 84 | 1 |
| 41.3 | 35 | 42 | 4 | 1 | 95 | | 32.5 | 36 | 37 | 16 | 1 | 98 | 0 |
| 50.3 | 30 | 59 | 20 | 1 | 91 | | 33.7 | 40 | 39 | 13 | 2 | 99 | 0 |
| 51.1 | 3 | 96 | 3 | 0 | 96 | | 35.8 | 3 | 66 | 37 | 0 | 99 | 0 |
| 65.2 | 3 | 91 | 14 | 0 | 99 | | 29.1 | 16 | 50 | 8 | 2 | 98 | 0 |
| 76.4 | 4 | 91 | 3 | 0 | 99 | | 71.0 | 41 | 56 | 3 | 0 | 100 | 0 |
| 67.8 | 32 | 62 | 34 | 0 | 86 | | 57.6 | 8 | 77 | 7 | 0 | 100 | 0 |
| 44.6 | 14 | 80 | 5 | 1 | 98 | | 97.5 | 65 | 32 | 1 | 2 | 99 | 0 |
| 59.1 | 28 | 42 | 29 | 1 | 97 | | 74.9 | 17 | 79 | 2 | 0 | 99 | 0 |
| 25.1 | 19 | 32 | 36 | 0 | 95 | | 35.4 | 14 | 24 | 36 | 0 | 99 | 0 |
| 21.2 | 56 | 24 | 29 | 1 | 97 | | 31.4 | 16 | 36 | 43 | 0 | 96 | 0 |
| 67.8 | 18 | 62 | 18 | 0 | 94 | | 43.1 | 6 | 32 | 4 | 1 | 99 | 0 |
| 42.9 | 17 | 75 | 7 | 0 | 98 | Average | 43.1 | 22.7 | 49.0 | 20.1 | 2.1 | 97.3 | 0.1 |
| 61.0 | 7 | 52 | 34 | 0 | 96 | St. Error | 4.0 | 3.8 | 4.9 | 3.4 | 0.9 | 0.9 | 0.0 |
| 50.6 | 23 | 76 | 5 | 0 | 92 | | | | | | | | |
| 27.2 | 19 | 45 | 33 | 0 | 98 | | | | | | | | |
| 43.9 | 9 | 47 | 31 | 0 | 97 | | | | | | | | |
| 30.8 | 4 | 50 | 41 | 0 | 99 | | | | | | | | |

TABLE 15-continued

| | NMA Treatment | | | | | | 6Gy TBI Treatment | | | | | |
|---|---|---|---|---|---|---|---|---|---|---|---|---|
| | Cells | TIL Pre Separation | | | Infusion Bag | | Cells | TIL Pre Separation | | | Infusion Bag | |
| | (x10e9) | CD4 | CD8 | NK | CD4 | CD8 | (x10e9) | CD4 | CD8 | NK | CD4 | CD8 | NK |
| | 31.0 | 26 | 12 | 53 | 0 | 98 | | | | | | | |
| | 44.8 | 1 | 55 | 46 | 0 | 96 | | | | | | | |
| | 5.8 | 80 | 8 | 3 | 8 | 88 | | | | | | | |
| | 47.6 | 6 | 81 | 19 | | | | | | | | | |
| Average | 47.7 | 21.8 | 57.2 | 20.8 | 0.8 | 96.0 | | | | | | | |
| St. Error | 3.3 | 3.2 | 4.3 | 2.6 | 0.3 | 0.6 | | | | | | | |

The CD8+ enrichment was highly effective for reducing the fraction of CD4+ cells in the infused TIL, as shown in Table 15. The CD4+ cell component comprised an average of 22% of the cells in bulk young TIL prior to CD8+ enrichment, and NK cells comprised 21% (Table 15). TIL from prior protocols administered without CD8+ enrichment after NMA conditioning also contained about 21% CD4+ cells. Following CD8+ enrichment and expansion, CD4+ cells were reduced to an average of 2% of the infused young TIL.

This example demonstrated a method of generating CD8+ enriched, "young" T cells, and also demonstrated that the CD8+ enrichment was highly effective for reducing the fraction of CD4+ cells in the infused TIL.

Example 13

This example demonstrates that the administration of CD8+ enriched, "young" T cells promotes the regression of cancer in human melanoma patients.

Patients, Clinical Samples and Trial Design

Patients were eligible for this study who were 18 years or older with measurable metastatic melanoma, at least one lesion respectable for TIL, good clinical performance, adequate liver and kidney function tests, blood counts near the normal range, free from active systemic infections without coagulation disorders or cardiovascular disease or immunodeficiency, negative for HIV antibody and hepatitis B and C, and a life expectancy of greater than three months. All patients signed an informed consent approved by the Institutional Review Board of the National Cancer Institute.

One group of 33 patients received non-myeloablative chemotherapy (NMA) consisting of 60 mg/kg/day cyclophosphamide for two days followed by five days of 25 mg/m²/day fludarabine. A second cohort of 23 patients received two days of 60 mg/kg cyclophosphamide overlapping the first two of five days of 25 mg/m²/day fludarabine. On the final day of fludarabine, patients received two fractions of 2Gy total body irradiation (TBI) separated by at least 6 hrs, and the following day they received one fraction of 2Gy TBI. On the day following chemotherapy or radiation all patients received a bolus intravenous infusion of CD8+ enriched young TIL (prepared generally as described in Example 12) and started high dose IL-2 therapy (720,000 IU/kg intravenously every 8 hrs to tolerance). The age (in days) of the CD8+ enriched young TIL administered to patients receiving NMA is as follows: 26, 27, 27, 28, 28, 29, 29, 30, 30, 30, 31, 31, 31, 31, 31, 32, 32, 34, 34, 34, 35, 35, 35, 35, 35, 36, 36, 37, 37, 41, 41, and 41 (average age is given in Table 16). The age (in days) of the CD8+ enriched young TIL administered to patients receiving TBI is as follows: 28, 29, 29, 30, 30, 30, 30, 31, 33, 33, 34, 35, 35, 35, 37, 37, 38, 38, 39, 42, 43, 47, and 53 (average age is given in Table 16).

One day after TIL infusion, patients who received 6Gy TBI received a minimum of $2 \times 10^6$/kg autologous purified (Miltenyi) CD34+ hematopoietic stem cells from a G-CSF+ plerixafor mobilized pheresis.

Patients received trimethoprim, sulfamethoxazole, and fungal prophylaxis following therapy; herpes virus seropositive patients also received valacyclovir. Platelets and packed red blood cells were administered as needed during hematopoietic recovery, and empiric antibiotics were initiated for neutropenic fevers (38.3° C. once or two temperatures of 38.0° C. at least one hour apart and absolute neutrophil count <500). Patient response was assessed using standard radiographic studies and physical examination at approximately four weeks following TIL administration and at regular intervals thereafter. The Response Evaluation Criteria In Solid Tumors (RECIST) guidelines were followed and patients were categorized into complete, partial, or non-responding categories. Complete blood counts (CBC) were obtained at least once per day while patients were in the hospital and differential counts were obtained when CBC was over 200 cells per microliter.

The demographic characteristics of these patients and the treatments administered are shown in Table 16.64% of patients had received prior IL-2. Median follow up in the NMA and 6Gy TBI cohorts was 14 months and 7 months, respectively.

TABLE 16

| | NMA | 6Gy TBI |
|---|---|---|
| Patients | 33 | 23 |
| Sex | | |
| Male | 14 | 13 |
| Female | 19 | 10 |
| Age (years) | | |
| ≤30 | 3 | 3 |
| 30-39 | 6 | 5 |
| 40-49 | 12 | 4 |
| 50-59 | 10 | 11 |
| ≥60 | 2 | 0 |
| HLA-A2+ | | |
| Yes | 11 | 10 |
| No | 22 | 13 |
| Prior IL-2 | | |
| Yes | 25 | 11 |
| No | 8 | 12 |
| Stage of disease | | |
| M1a | 2 | 1 |
| M1b | 11 | 10 |
| M1c | 20 | 12 |
| *Cell number (x10⁹) | 47.7 (±3.3) | 43.1 (±7.5) |

TABLE 16-continued

|  | NMA | 6Gy TBI |
| --- | --- | --- |
| IL-2 (doses) | 6.3 (±0.3) | 7.5 (±0.5) |
| Average Age of cells at Infusion (days) | 32.7 (±0.7) | 35.4 (±1.3) |
| CD4+ cells (%) |  |  |
| Prior to CD8+ enrichment | 21.8 (±3.2) | 22.7 (±3.6) |
| Infused | 0.6 (±0.3) | 2.1 (±0.8) |
| CD8+ cells (%) |  |  |
| Prior to CD8+ enrichment | 57.2 (±4.3) | 49.0 (±4.7) |
| Infused | 96.0 (±0.6) | 97.3 (±0.8) |
| Tissue of TIL origin† |  |  |
| Lymph node | 16 | 6 |
| Subcutaneous | 10 | 7 |
| Liver | 4 | 3 |
| Lung | 3 | 5 |
| Large bowel | 0 | 1 |
| Intramuscular | 0 | 2 |
| Other visceral site | 2 | 1 |

*Average (±Standard Error)
†Some patients were treated with TIL from multiple tissues of origin Nineteen of the 33 patients (58%) in the NMA cohort exhibited an objective tumor regression by RECIST criteria, including 16 partial responders (48%), and 3 complete responders (9%). Eleven of 23 patients (48%) in the 6Gy TBI cohort achieved an objective response, including two complete responders (9%).

Figure 4:
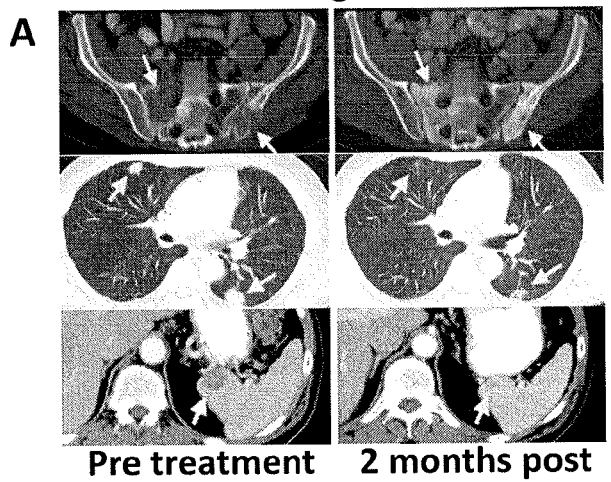
FIG. 4A is a computed tomography (CT) scan showing metastatic melanoma lesions (arrows) in a first patient before CD8+ enriched young TIL therapy in the sacrum and ilium (top left), lung (middle left) and spleen (lower left) and 2 months after treatment in the sacrum and ilium (top right), lung (middle right) and spleen (lower right).
FIG. 4B (left panel) is a photograph showing subcutaneous melanoma around the ear and in the auditory canal in a second patient nine days prior to CD8+ enriched young TIL therapy; middle panel is a photograph showing gross necrosis of the melanoma 11 days following treatment; right panel is a photograph showing a partial response 76 days after treatment.
FIG. 4C (left panel) is a CT scan showing (from top to bottom) mediastinal, lung, nodal and subcutaneous metastatic deposits (arrows) in a third patient before (left) and one month after (right) treatment with CD8+ enriched young TIL.
Figure 4:
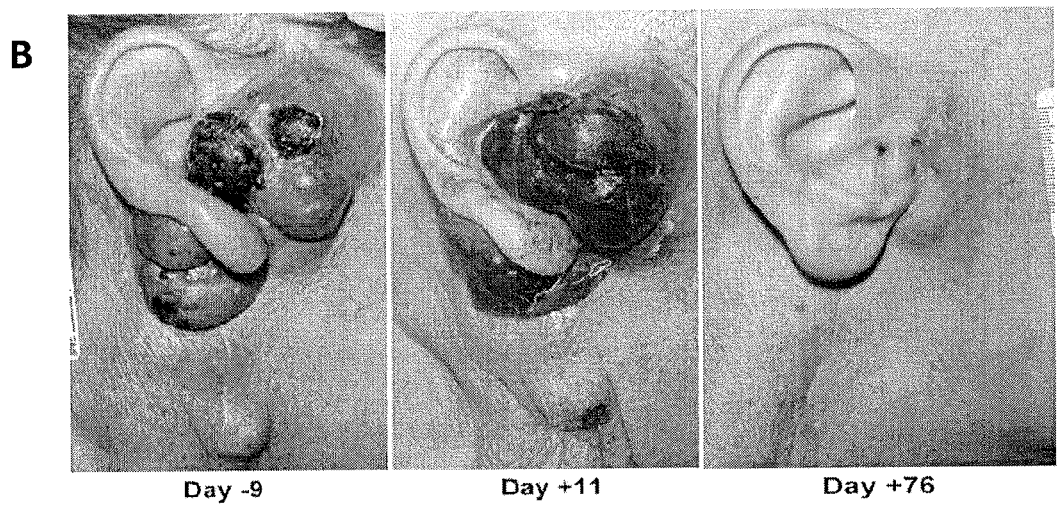
Figure 4:
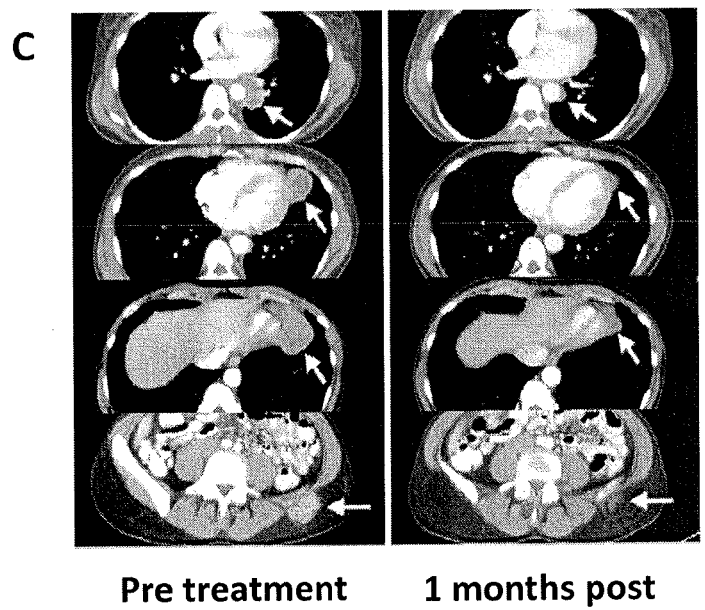

Illustrative examples of clinical tumor regression are shown in FIGS. 4A, 4B, and 4C. CD8+ enriched young TIL caused regression of bulky melanoma lesions at multiple sites. FIG. 4A shows CT scans of metastatic melanoma lesions (arrows) in a first patient before CD8+ enriched young TIL therapy in the sacrum and ilium (top left), lung (middle left) and spleen (lower left). As shown in FIG. 4A, all lesions showed regression at two months (right) with visible signs of recalcification of prior metastatic sites in the sacrum and ilium. FIG. 4B (left panel) is a photograph showing subcutaneous melanoma around the ear and in the auditory canal that caused complete hearing loss in a second patient. FIG. 4B (middle panel) is a photograph showing that eleven days after CD8+ enriched young TIL infusion, gross necrosis of the melanoma was visible. FIG. 4B (right panel) is a photograph showing that at 76 days after treatment, the patient experienced a partial response at all sites including liver and subcutaneous lesions. Tumor was absent from the auditory canal and the patient's hearing returned to normal. FIG. 4C shows CT scans illustrating mediastinal, lung, nodal and subcutaneous metastatic deposits in a third patient before (Left) and one month after (Right) treatment with CD8+ enriched young TIL, demonstrating the rapid initial pace of tumor regression in a patient who eventually achieved a complete response.

Fifteen of 24 patients with M1a or M1b melanoma and 15 out of 32 patients with M1c disease responded to therapy. As reported previously (Dudley et al. *J. Clin. Oncol.* 26(32): 5233-9 (2008); Dudley et al. *J. Clin. Oncol.* 23(10):2346-57 (2005)) all patients experienced transient hematological toxicities from the lymphodepleting conditioning and received platelet and red blood cell transfusions as medically indicated. Patients were also treated for symptoms associated with high dose IL-2 therapy. All toxicities typically returned to baseline within a few days. All non-hematological grade 3 and 4 toxicities not attributable to IL-2 are listed in Table 17. There were no Grade 3 or 4 toxicities directly attributable to the infused cells. There were two treatment related mortalities, one in each cohort that resulted from acute sepsis during the neutropenic period associated with lymphodepletion about five days after TIL infusion.

TABLE 17

|  | NMA | 6Gy TBI | Total |
| --- | --- | --- | --- |
| Total Patients | 33 | 23 | 56 |
| Clinical Responses (RECIST) |  |  |  |
| Non-response | 14 (42%) | 12 (52%) | 26 (46%) |
| Partial Response | 16 (48%) | 9 (39%) | 25 (45%) |
| Durations (months) | 16+, 15+, 14+, 14, 13+, 13, 12, 10, 9, 8, 8, 7, 6, 5, 3, 2 | 9+, 8+, 6, 5+, 4+, 4+, 4, 3, 2 |  |
| Complete Response | 3 (9%) | 2 (9%) | 5 (9%) |
| Durations (months) | 18+, 15+, 12+ | 5+, 5+ |  |
| Toxicities† |  |  |  |
| Positive blood culture | 8 | 4 | 12 (21%) |
| Febrile neutropenia (Grade 3) | 17 | 11 | 28 (50%) |
| Intubation | 2 | 2 | 4 (7%) |
| Treatment related death | 1 | 1 | 2 (4%) |

†Listed once for each patient at the highest grade. Usual IL-2 related toxicities not listed.

The age of TIL was compared for patients who received CD8+ enriched TIL and patients on prior TIL protocols (FIG. 5B). Prior protocols required all TIL to undergo individualized testing for tumor reactivity (Specific TIL, n=92). TIL from non-responding patients (n=40, NR) spent significantly longer time in culture prior to administration than TIL from objective responders (n=52, OR). There was no difference (NS) between the time spent in culture of CD8+ enriched young TIL (Young TIL) administered to non-responding patients (n=26) or responders (n=30). Microculture generated, tumor-selected TIL administered to responding patients were significantly younger than TIL given to patients who did not respond. In the cohorts treated in Example 13, there was no difference between the age of CD8+ enriched young TIL cultures for responding and non-responding patients, but these cultures were significantly younger than TIL cultures administered on prior protocols ($p2=3\times10^{-7}$).

This example demonstrated that the administration of CD8+ enriched, "young" T cells promotes the regression of cancer in human melanoma patients.

Example 14

This example demonstrates that the generation of "young" TIL for treatment is reliable and rapid.

176 tumors from 122 patients were processed to establish young TIL cultures, as described in Example 12. TIL were successfully grown ($>50\times10^6$ cells within five weeks) from 124 of the 176 lesions (70%), comprising 101 of the 122 patients (83%).

Specimens from 122 sequential patients who were eligible for TIL therapy were processed to single cell suspensions. The fraction of lymphocytes among viable cells was determined by morphological criteria after trypan blue staining. The samples were plotted in FIG. 5A based on whether sufficient TIL grew to use for treatment ($>5\times10^7$ cells in 28 days, Rx TIL) or whether growth was insufficient for treatment (No growth). A striking correlation was observed between the success of establishing TIL and the initial proportion of lymphocytes in the single cell suspension (FIG. 5A). Tumors that successfully yielded TIL had an initial median of 52% lymphocytes while tumors that failed to grow in vitro had a median of 8% lymphocytes (p2=5×10$^{-8}$).

Among these 122 patients, 53 patients were treated (three additional patients received cryopreserved TIL from prior resections), 21 patients had samples that failed to grow TIL cultures, 20 patients developed rapidly progressive disease that prevented treatment, 13 patients were resected free of evaluable disease (although nine patients recurred and received TIL treatment subsequently), nine patients received other treatments including one complete responder to high dose IL-2 therapy, and six patients experienced individual laboratory or clinical issues, including exactly one patient whose CD8+ TIL failed to expand during the rapid expansion protocol (REP).

This example demonstrated that bulk TIL were generated within five weeks prior to rapid expansion for 83% of the patients studied, and that the percent of lymphocytes in the initial single cell suspension correlated with TIL growth.

Example 15

This example demonstrates that an objective response can be obtained using CD8+ enriched, "young" TILs that do not exhibit tumor recognition in vitro.

The ability of the administered CD8+ enriched TIL to recognize tumor was retrospectively evaluated, looking for any correlation with clinical efficacy. Recognition of autologous or HLA-matched tumor was evaluated by cytokine release assay for CD8+ enriched young TIL administered to patients after NMA conditioning (FIG. 6A) or for CD8+ enriched young TIL administered to patients after 6Gy TBI conditioning (FIG. 6B). TIL from cryopreserved aliquots of each infused treatment was thawed and rested overnight in IL-2, then washed and incubated at a 1:1 ratio with autologous, HLA-matched, or HLA-mismatched tumors. Interferon (IFN)-gamma secreted in the coculture supernatant was quantified by ELISA. The data from each separate coculture assay was aggregated and plotted (FIGS. 6A and 6B).

Twenty-three of the 33 NMA patients had autologous tumor available (18 with cryopreserved tumor digest and 5 with a tumor cell line). Eight of 10 non-responding patients and 8 of 13 objective responders demonstrated autologous tumor recognition. Four additional objective responding patients recognized HLA-A matched tumor cell lines. Nineteen of 23 patients treated with 6Gy TBI had autologous tumor available (15 with fresh frozen tumor, and four with a cell line). 8 of 11 non-responding patients and 5 of 8 responding patients demonstrated specific tumor recognition. In addition, three patients' TIL recognized HLA-matched tumor cell lines, including one non-responding patient (SA) whose TIL failed to recognize autologous tumor. In total, 29 of 42 evaluable CD8+ enriched young TIL samples (69%) demonstrated specific autologous tumor recognition and 36 of 56 (64%) patients demonstrated specific recognition at all. Strikingly, 11 of 30 objective responses were mediated by CD8+ enriched young TIL with no evidence of specific tumor recognition as defined in prior TIL clinical protocols.

Previously, ninety-three patients were treated over 84 months using highly expanded TIL selected for specific tumor recognition (Dudley et al. *J. Clin. Oncol.* 26(32):5233-9 (2008)), corresponding to about one treatment per month and about 27% of resected patients who finally received a TIL product. As described in Example 13, 56 additional patients were treated with CD8+ enriched young TIL over 14 months, corresponding to about 3 to 4 patients treated per month with 53% of eligible patients who underwent resection able to receive TIL therapy. With both methods, clinical response rates were about 55%, but 11 objective responders out of 30 in the study described in Example 13 had TIL that would have been ineligible for the prior study.

This example demonstrated that 11 of 30 objective responses were mediated by CD8+ enriched young TIL that did not demonstrate tumor reactivity in vitro.

Example 16

This example demonstrates that CD8+ enriched, "young" TIL exhibit a higher capacity for in vivo expansion compared to selected TIL.

The average absolute lymphocyte count (ALC) for all patients who received CD8+ enriched young TIL after NMA or 6Gy TBI lymphodepletion was determined daily and is plotted in FIGS. 7A and 7B, respectively. Not all patients had ALC determined every day. For comparison, lymphocyte reconstitution from patients who received antigen selected TIL derived from microculture expansions after NMA or 12Gy TBI (Dudley et al. *J. Clin. Oncol.* 26(32):5233-9 (2008)) lymphodepletion are also shown. As shown in FIGS. 7A and 7B, CD8+ enriched young TIL quickly repopulated patient peripheral blood to high levels after NMA or 6Gy TBI conditioning. Interestingly, patients who received CD8+ enriched young TIL demonstrated higher peak ALC's, suggesting that CD8+ enriched young TIL have increased capacity for in vivo expansion compared to selected TIL.

Example 17

This example demonstrates that there is an increase in CD8+ ALC in responding patients compared to non-responders approximately one month after cell infusion.

CD4+ and CD8+ ALC was determined in a blinded manner by the Clinical Center Core Immunology Laboratory for 47 of 56 patients treated with CD8+ enriched young TIL at approximately one month after TIL infusion. PBL from 47 of the 56 patients who received CD8+ enriched young TIL were sampled at approximately one month after cell infusion. ALC and absolute CD3+ CD8+ and CD3+ CD4+ cell numbers were assessed by FACS analysis in a blinded manner. The treatment resulted in low CD4 counts at one month in most patients (average: 109 CD4+ cells/up, with no difference between responding and non-responding patients (p2=0.5; FIG. 7D). Patients in prior clinical trials who received TIL that contained CD4+ lymphocytes had higher peripheral CD4+ cell counts at one month after TIL infusion (average: 187 cells/ul). In contrast to CD4+ cells, CD8+ ALC for most patients treated with CD8+ enriched young TIL was in the normal range at one month, and there was a significant increase in CD8+ ALC in responding patients compared to non-responders (p2=0.002; FIG. 7C). Patients who responded had CD8+ ALC about two fold higher than non-responders (1504 vs. 696 cells/up. In prior clinical trials, the average CD8+ cell count was 652 CD8+ cells/ul at one month after TIL infusion. Infused TIL were examined by FACS for expression of additional markers including CD27, CD28, CD62L, CCR7, but none correlated with clinical response.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of generating a T cell infusion product for promoting regression of a cancer in a mammal, the method comprising:
   (i) culturing autologous T cells;
   (ii) enriching the cultured T cells for CD8+ T cells;
   (iii) expanding the number of cultured T cells using OKT3 antibody, IL-2, and feeder lymphocytes to provide an expanded number of T cells that are about 19 to about 35 days old; and
   (iv) providing the expanded number of T cells that are about 19 to about 35 days old as a cell infusion product,
   wherein (ii) is performed prior to (iii), the T cells have not been screened for specific tumor reactivity, and the T cells recognize an antigen of a cancer.

2. The method according to claim 1, comprising producing T cells having a higher expression of CD27 as compared to T cells that are about 44 days old.

3. The method of claim 1, comprising modifying the T-cells to express a T-cell growth factor that promotes the growth and activation of the autologous T-cells.

4. The method of claim 1, comprising modifying the T cells to express a T cell receptor having antigenic specificity for a cancer antigen.

5. The method according to claim 1, comprising producing T cells having a higher expression of CD28 as compared to T cells that are about 44 days old.

6. The method according to claim 1, comprising producing T cells having a mean telomere length that is longer than that of T cells that are about 44 days old.

7. The method according to claim 1, comprising producing T cells having a higher frequency of CD4+ cells as compared to T cells that are about 44 days old.

8. The method according to claim 1, comprising providing an expanded number of T cells that are about 19 to about 26 days old.

9. The method according to claim 1, comprising providing an expanded number of T cells that are about 19 to about 29 days old.

10. The method according to claim 1, comprising providing an expanded number of T cells that are about 23 to about 29 days old.

11. The method according to claim 1, wherein the T cells are capable of promoting regression of a cancer in a mammal.

* * * * *